US009557290B2

(12) United States Patent
Cheng et al.

(10) Patent No.: US 9,557,290 B2
(45) Date of Patent: Jan. 31, 2017

(54) NANOCHANNEL ELECTRODE DEVICES

(71) Applicant: GLOBALFOUNDRIES INC., Grand Cayman (KY)

(72) Inventors: Kangguo Cheng, Schenectady, NY (US); Joseph Ervin, Slingerlands, NY (US); Juntao Li, Cohoes, NY (US); Chengwen Pei, Danbury, CT (US); Geng Wang, Stormville, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 0 days.

(21) Appl. No.: 14/987,329

(22) Filed: Jan. 4, 2016

(65) Prior Publication Data

US 2016/0116435 A1    Apr. 28, 2016

Related U.S. Application Data

(62) Division of application No. 14/452,741, filed on Aug. 6, 2014, now Pat. No. 9,228,994.

(51) Int. Cl.

| H01L 29/08 | (2006.01) |
| G01N 27/414 | (2006.01) |
| G01N 33/487 | (2006.01) |
| H01L 29/41 | (2006.01) |
| H01L 21/84 | (2006.01) |
| H01L 27/12 | (2006.01) |

(52) U.S. Cl.
CPC .... *G01N 27/4145* (2013.01); *G01N 33/48721* (2013.01); *H01L 21/845* (2013.01); *H01L 27/1211* (2013.01); *H01L 29/0847* (2013.01); *H01L 29/413* (2013.01)

(58) Field of Classification Search
CPC ............... G01N 27/4145; G01N 33/48721; H01L 29/413; H01L 21/845; H01L 27/1211; H01L 29/0847
See application file for complete search history.

(56) References Cited

U.S. PATENT DOCUMENTS

| 6,515,847 B1 | 2/2003 | Naraya |
| 6,627,067 B1 | 9/2003 | Branton et al. |
| 6,638,885 B1 | 10/2003 | McGrath et al. |

(Continued)

OTHER PUBLICATIONS

Meller, A. et al., "Rapid nanopore discrimination between single polynucleotide molecules" PNAS (Feb. 1, 2000) pp. 1079-1084, vol. 97, No. 3.

(Continued)

*Primary Examiner* — Long Pham
(74) *Attorney, Agent, or Firm* — Scully, Scott, Murphy & Presser, P.C.

(57) ABSTRACT

A nanoscale electrode device can be fabricated by forming a pair of semiconductor fins laterally spaced from each other by a uniform distance and formed on a substrate. The pair of semiconductor fins can function as a pair of electrodes that can be biased to detect the leakage current through a nanoscale string to pass therebetween. A nanochannel having a uniform separation distance is formed between the pair of semiconductor fins. The nanochannel may be defined by a gap between a pair of raised active regions formed on the pair of semiconductor fins, or between proximal sidewalls of the pair of semiconductor fins. An opening is formed through the portion of the substrate underlying the region of the nanochannel to enable passing of a nanoscale string.

10 Claims, 23 Drawing Sheets

(56) References Cited

U.S. PATENT DOCUMENTS

| | | |
|---|---|---|
| 6,960,298 B2 | 11/2005 | Krotz et al. |
| 7,045,851 B2 | 5/2006 | Black et al. |
| 7,098,393 B2 | 8/2006 | Fleurial et al. |
| 7,217,562 B2 | 5/2007 | Cao et al. |
| 7,223,894 B2 | 5/2007 | Chau et al. |
| 7,248,771 B2 | 7/2007 | Schmidt et al. |
| 7,250,544 B2 | 7/2007 | Chau et al. |
| 7,274,078 B2 | 9/2007 | Jaiprakash et al. |
| 7,444,053 B2 | 10/2008 | Schmidt et al. |
| 7,582,490 B2 | 9/2009 | Golovchenko et al. |
| 7,586,618 B2 | 9/2009 | Marks et al. |
| 7,610,074 B2 | 10/2009 | Boppart et al. |
| 7,623,908 B2 | 11/2009 | Boppart et al. |
| 7,626,246 B2 | 12/2009 | Lochtefeld et al. |
| 8,384,195 B2 | 2/2013 | Wang et al. |

OTHER PUBLICATIONS

Sanderson, K., "Standard and Pores, Could the next Generation of Genetic Sequencing machines be built from a collection of miniscule holes?" Nature (Nov. 6, 2008) pp. 23-25, vol. 456.

Li, J. et al., "Ion-beam sculpting at nanometre length scales" Nature (Jul. 12, 2001) pp. 166-169, vol. 412, No. 6843.

"IBM Research Aims to Build Nanoscale DNA Sequencer to Help Drive Down Cost of Personalized Genetic Analysis: IBM scientists advance genome sequencing project" Yorktown Heights, NY (Oct. 6, 2009) https://www-03.ibm.com/press/us/en/pressrelease/28558.wss.

NANOCHANNEL ELECTRODE DEVICES

RELATED APPLICATION

This application is a divisional of U.S. Ser. No. 14/452,741, filed Aug. 6, 2014, the entire contents of which are incorporated herein by reference.

BACKGROUND

The present disclosure relates to nanochannel electrode devices, and more particularly to electrode devices including a pair of electrodes laterally separated by a nanochannel, and a method of manufacturing the same.

Determination of electrical properties of a nanoscale string is useful in determining molecular structures of the nanoscale string. For example, determination of electrical properties of a DNA string can provide information on the sequence of the molecules within the DNA string, and enable decoding of the DNA sequence within the DNA string. In order to reliably measure properties of the nanoscale string employing a pair of electrodes, it is necessary that the electrode spacing be well defined with little error. In order to facilitate the passing of the nanoscale string between the pair of electrodes, it is desirable that the length of the opening between the pair of electrodes be significantly longer than the width of the opening. Thus, an electrode device is desired that can provide direct reading of electrical properties of the molecules within a nanoscale string along the lengthwise direction as the nanoscale string passes through a nanochannel having a well defined uniform width and a length L that is significantly greater than the uniform width.

SUMMARY

A nanoscale electrode device can be fabricated by forming a pair of semiconductor fins laterally spaced from each other by a uniform distance and formed on a substrate. The pair of semiconductor fins can function as a pair of electrodes that can be biased to detect the leakage current through a nanoscale string to pass therebetween. A nanochannel having a uniform separation distance is formed between the pair of semiconductor fins. The nanochannel may be defined by a gap between a pair of raised active regions formed on the pair of semiconductor fins, or between proximal sidewalls of the pair of semiconductor fins. Optionally, one or more additional semiconductor fins may be placed between the pair of semiconductor fins such that raised active regions provide self-aligned edges defining the length of the nanochannel. Optionally, one or more dummy gate structures may be employed to define self-aligned edges defining the length of the nanochannel. An opening is formed through the portion of the substrate underlying the region of the nanochannel to enable passing of a nanoscale string. A semiconductor-on-insulator (SOI) substrate or a bulk substrate may be employed to form the nanoscale electrode device.

According to an aspect of the present disclosure, a structure includes a pair of parallel electrodes located on a substrate. Each of the pair of parallel electrodes includes at least a semiconductor fin, and a nanochannel is present between the pair of parallel electrodes. The structure further includes a metal interconnect structure-containing layer including conductive structures embedded in at least one dielectric material layer. Each of the conductive structures is electrically shorted to one of the pair of parallel electrodes. The structure further includes a contiguous cavity passing through the substrate and the at least one dielectric material layer. The contiguous cavity includes the nanochannel.

According to another aspect of the present disclosure, a method of forming a structure is provided. A pair of parallel electrodes is formed on a substrate. Each of the pair of parallel electrodes includes at least a semiconductor fin. A nanochannel is formed between the pair of parallel electrodes. A metal interconnect structure-containing layer is formed, which includes conductive structures embedded in at least one dielectric material layer. Each of the conductive structures is electrically shorted to one of the pair of parallel electrodes. A contiguous cavity passing through the substrate and the metal interconnect structure-containing layer is formed. The contiguous cavity includes the nanochannel.

DETAILED DESCRIPTION

Figure 1A:
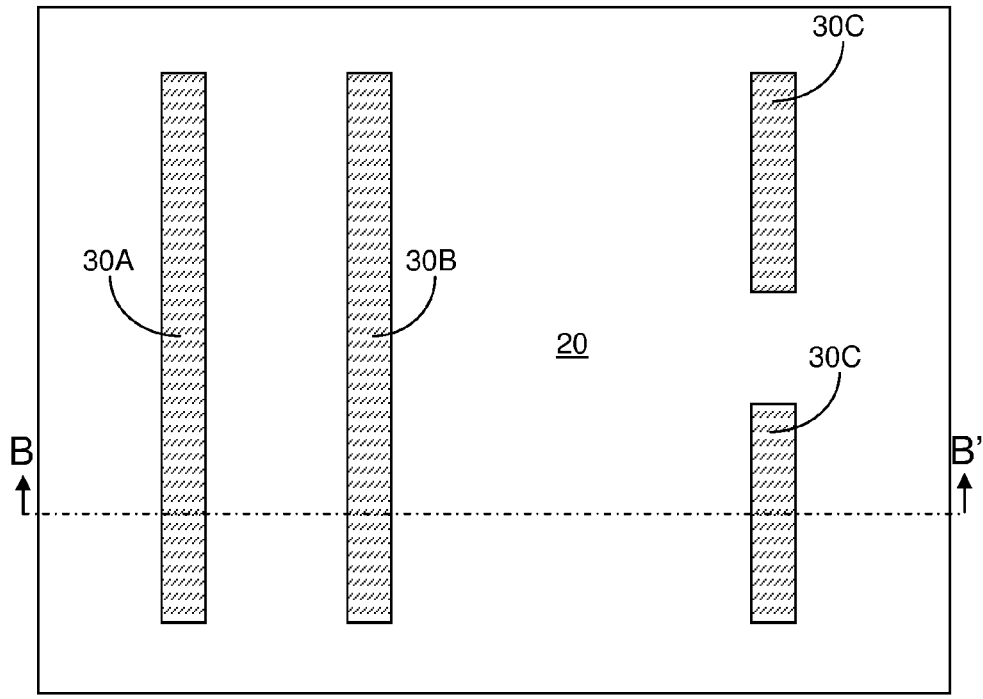
FIG. 1A is a top-down view of a first exemplary structure including semiconductor fins formed on an insulator layer according to a first embodiment of the present disclosure.

As stated above, the present disclosure relates to electrode devices including a pair of electrodes laterally separated by a nanochannel, and a method of manufacturing the same. Aspects of the present disclosure are now described in detail with accompanying figures. It is noted that like reference numerals refer to like elements across different embodiments. The drawings are not necessarily drawn to scale.

As used herein, a structural element is referred to as being "on" another structural element when the structural element is located directly on the other structural element or when a set of at least one intervening element making direct physical contact with the structural element and the other structural element is present. A structural element is referred to as being "directly on" another structural element when there is no intervening structural element and a physical contact is formed between the structural element and the other structural element. Likewise, an element is referred to as being "connected" or "coupled" to another element when the element is directly connected or coupled to the other element or when a set of at least one intervening element provides connection or coupling with the element and the other element. An element is referred to as being "directly connected" or "directly coupled" to another element when there is no intervening element and the connection or coupling is provided between the element and the other element. An element "abuts" another element when a physical interface area providing a direct contact is present between the element and the other element.

Figure 1B:
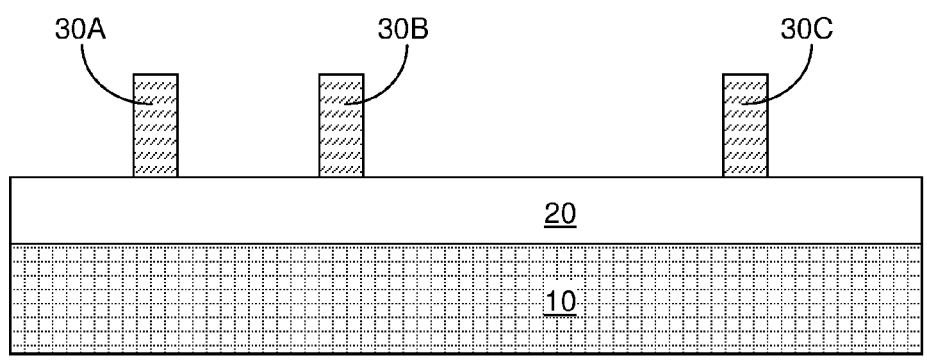
FIG. 1B is a vertical cross-sectional view of the first exemplary structure along the vertical plane B-B' of FIG. 1A.

Referring to FIGS. 1A and 1B, a first exemplary structure according to a first embodiment of the present disclosure includes semiconductor fins (30A, 30B, 30C) formed on an insulator layer 20. In one embodiment, the semiconductor fins (30A, 30B, 30C) can be formed by providing a semiconductor-on-insulator (SOI) substrate including a handle substrate 10, an insulator layer 20 (which is commonly referred to as a buried insulator layer), and a top semiconductor layer including a semiconductor material, and by patterning the top semiconductor layer into the semiconductor fins (30A, 30B, 30C) employing methods known in the art. The semiconductor material of the semiconductor fins (30A, 30B, 30C) is herein referred to as a first semiconductor material. The first semiconductor material can be an elemental semiconductor material or an alloy thereof, a compound semiconductor material, or an organic semiconductor material. In one embodiment, the first semiconductor material can be a single crystalline semiconductor material. In one embodiment, the first semiconductor material can be single crystalline silicon, a single crystalline silicon-germanium alloy, a single crystalline silicon-carbon alloy, or a single crystalline silicon-germanium-carbon alloy. Various portions of the semiconductor fins (30A, 30B, 30C) may be doped with different dopant types and/or at different dopant concentrations as needed.

Each semiconductor fin (30A, 30B, or 30C) can have a parallel pair of lengthwise sidewalls and a parallel pair of end walls. The parallel pair of lengthwise sidewalls is parallel to the lengthwise direction of the semiconductor fin (30A, 30B, or 30C). As used herein, the lengthwise direction is the horizontal direction which passes through the center of mass of an element and around which the moment of inertia of the elements is at the minimum. The parallel pair of end walls can be perpendicular to the lengthwise direction for each semiconductor fin (30A, 30B, 30C). The width of each semiconductor fin (30A, 30B, or 30C), as measured along the horizontal direction perpendicular to the lengthwise direction of the semiconductor fin (30A, 30B, or 30C), can be in a range from 5 nm to 80 nm, although lesser and greater widths can also be employed. The height of each semiconductor fin (30A, 30B, or 30C) can be in a range from 5 nm to 200 nm, although lesser and greater heights can also be employed. The semiconductor fins (30A, 30B, 30C) can include a parallel pair of semiconductor fins (30A, 30B) that are subsequently employed as portions of a parallel pair of electrodes, and can include device semiconductor fins 30C, which can be employed to form conventional semiconductor devices as known in the art (such as fin field effect transistors). As used herein a device semiconductor fin refers to a semiconductor fin to form fin-based semiconductor devices as known in the art.

Figure 2A:
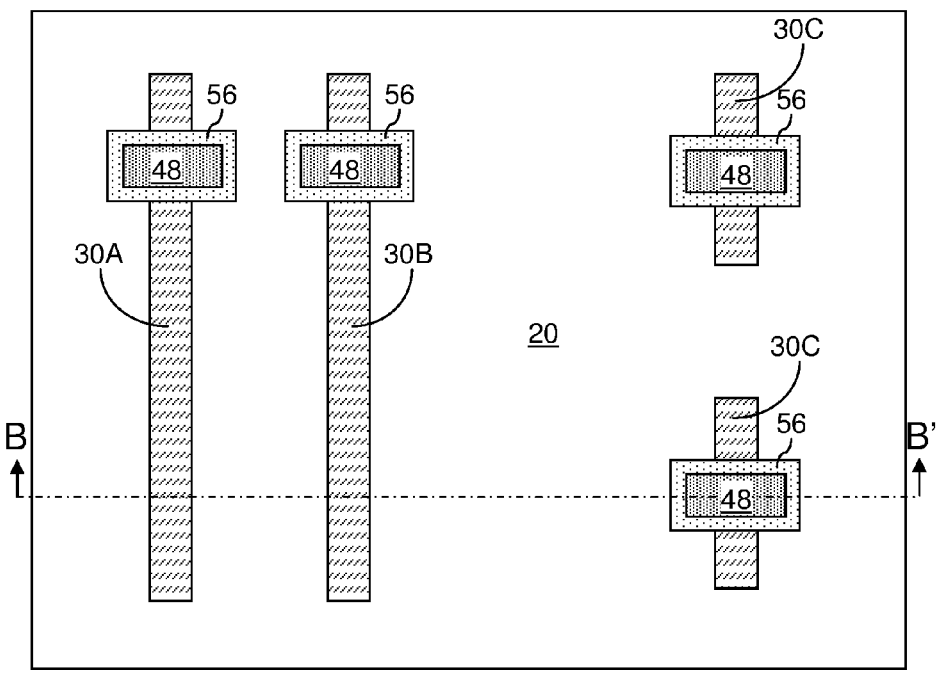
FIG. 2A is a top-down view of the first exemplary structure after formation of various gate structures according to the first embodiment of the present disclosure.
Figure 2B:
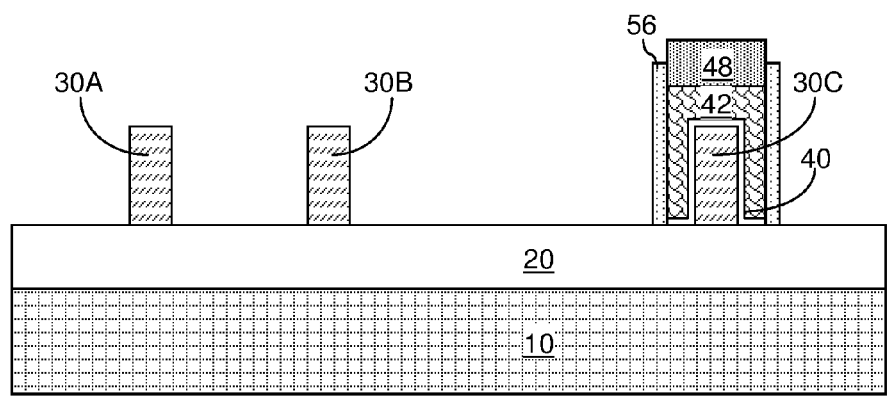
FIG. 2B is a vertical cross-sectional view of the first exemplary structure along the vertical plane B-B' of FIG. 2A.

Referring to FIGS. 2A and 2B, gate structures (40, 42, 48, 56) are formed across one or more of the semiconductor fins (30A, 30B, 30C). Each gate structure (40, 42, 48, 56) can include a gate dielectric 40 and a gate electrode 42, and can optionally include a gate dielectric cap 48 and/or a gate spacer 56 including a dielectric material. In one embodiment, a gate structure (40, 42, 48, 56) can be formed across at least one of the semiconductor fins (30A, 30B) among the parallel pair of semiconductor fins (30A, 30B). In one embodiment, a gate structure (40, 42, 48, 56) can be formed across each of the semiconductor fins (30A, 30B) among the parallel pair of semiconductor fins (30A, 30B). In one embodiment, the gate structures (40, 42, 48, 56) may not be formed across the parallel pair of semiconductor fins (30A, 30B). If the gate structures (40, 42, 48, 56) are not formed across the first and second semiconductor fins (30A, 30B), the entirety of each of the first and second semiconductor fins (30A, 30B) can be doped with dopants of the same conductivity type, which can be p-type or n-type, so that the entirety of each semiconductor fin (30A, 30B) is a conductive structure.

The gate dielectrics 40, the gate electrodes 42, and the optional gate dielectric caps 48 may be formed as permanent structures (i.e., structures that are present in original form at the end of the sequence of processing steps that completes the first exemplary structure), or can be formed as temporary structures that are replaced with permanent structures that include a replacement gate dielectric and a replacement gate electrode employing a sequence of processing steps known as the replacement gate integration scheme. The gate dielectrics 40 can include a dielectric material such as silicon oxide, silicon oxynitride, and/or a high dielectric constant (high-k) dielectric material including a dielectric metal oxide. The gate electrodes 42 can include a conductive material such as a doped semiconductor material and/or a metallic material. If the gate electrodes 42 are formed as temporary structures to be replaced with permanent replacement gate electrodes at a later processing step, the gate electrodes 42 may employ a non-conductive material. Further, the gate dielectrics 40 are formed as temporary structures, the gate dielectrics 40 may be replaced with a different disposable structure that can be removed selective to the semiconductor material of the semiconductor fins (30A, 30B, 30C).

Figure 3A:
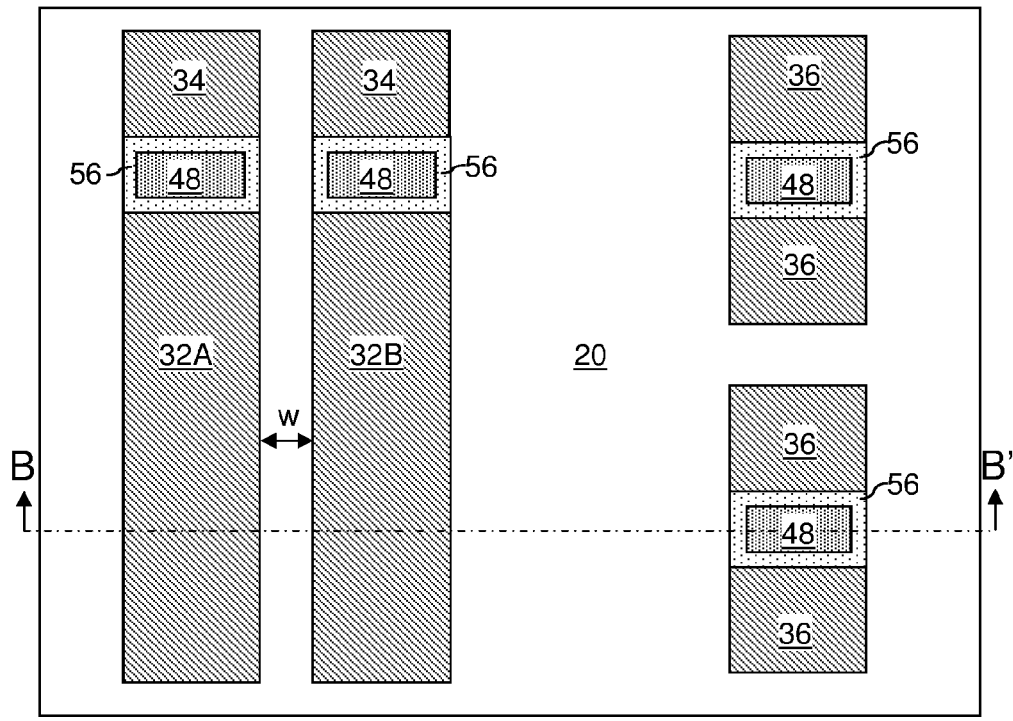
FIG. 3A is a top-down view of the first exemplary structure after formation of raised active regions according to the first embodiment of the present disclosure.
Figure 3B:
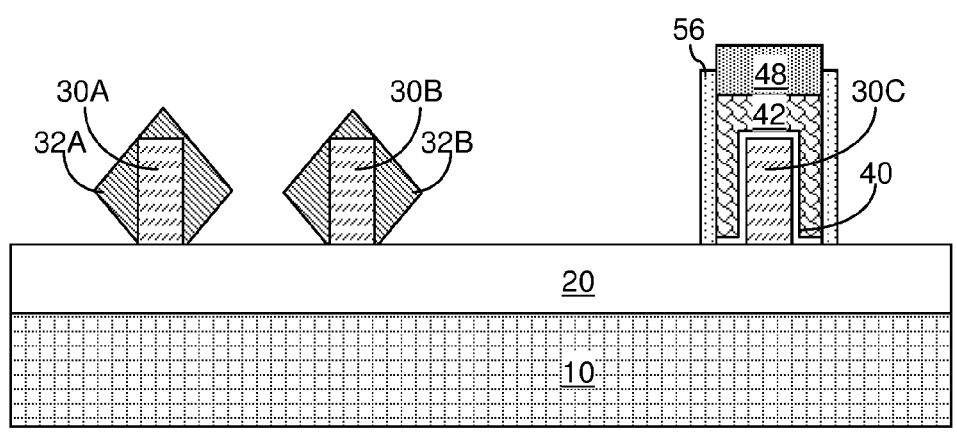
FIG. 3B is a vertical cross-sectional view of the first exemplary structure along the vertical plane B-B' of FIG. 3A.

Referring to FIGS. 3A and 3B, a selective deposition process can be optionally performed to form various raised semiconductor regions, which can be subsequently doped or in-situ doped during the selective deposition process to form various raised active regions (32A, 32B, 34, 36). As used herein, an "active region" refers to a doped semiconductor material portion. As used herein, a "raised active region" refers to a doped semiconductor material portion that is formed on a surface of a semiconductor fin. The selective deposition process deposits a semiconductor material, which is herein referred to as a second semiconductor material, on semiconductor surfaces while preventing deposition of the second semiconductor material on dielectric surfaces.

During the selective deposition process, a reactant gas that deposits the second semiconductor material and an etchant gas that etches the second semiconductor material are flowed simultaneously or alternately so that the net deposition rate of the second semiconductor material on crystalline surfaces is positive, while the net deposition rate of the second semiconductor material on amorphous surfaces is zero. The selective deposition process utilizes the growth rate differential of the second semiconductor material on crystalline surfaces and amorphous surfaces. It is well known that the growth rate of semiconductor materials is less on amorphous surfaces during a nucleation phase because nucleation of a semiconductor material on an amorphous surface proceeds at a much lower rate than deposition of the same semiconductor material on crystallographic surfaces due to kinematics of the growth process. In order to enable the selective deposition process, the flow rate of the etchant gas is selected such that the etch rate of the second semiconductor material is less than the deposition rate of the second semiconductor material on crystalline surfaces and is greater than the nucleation rate of the second semiconductor material on dielectric surfaces.

In one embodiment, the selective deposition process can be a selective epitaxy process that deposits the second semiconductor material. The second semiconductor material can be any semiconductor material that can be deposited as a single crystalline material or a polycrystalline material. The second semiconductor material may be the same as, or may be different from, the first semiconductor material. In one embodiment, the second semiconductor material can be single crystalline, in which can the second semiconductor material in the various raised active regions (32A, 32B, 34, 36) can be epitaxially aligned to the semiconductor fins (30A, 30B, 30C). Various portions of the semiconductor fins (30A, 30B, 30C) may be doped suitably prior to, or after, the selective deposition process. For example, fin source regions (not shown) and fin drain regions (not shown) can be formed in various portions of the semiconductor fins (30A, 30B, 30C) by ion implantation and/or diffusion from the raised active regions (32A, 32B, 34, 36) and/or by other methods known in the art. As used herein, fin source regions and fin drain regions refer to portions of source regions and portions of drain region that are present within semiconductor fins.

The selective deposition process may deposit the second semiconductor material as an intrinsic semiconductor material, or as a doped semiconductor material. The second semiconductor material can be subsequently doped by introduction of p-type dopants and/or n-type dopants, for example, by ion implantation. In one embodiment, portions of semiconductor fins (30A, 30B, 30C) that underlie gate structures (40, 42, 48, 56) can constitute body regions of field effect transistors.

The raised active regions (32A, 32B, 34, 36) include a first raised active region 32A formed on at least a portion of the first semiconductor fin 30A, and a second raised active region 32B formed on at least a portion of the second semiconductor fin 30B. At least one additional raised active region 34 can be formed on the first and/or second semiconductor fins (30A, 30B) if at least one gate structure (40, 42, 48, 56) is present on the first and/or second semiconductor fins (30A, 30B). Device raised active regions 36, i.e., raised active regions that are employed as an element of a semiconductor device as known in the art, can be formed on device semiconductor fins 30C. In an embodiment in which gate structures (40, 42, 48, 56) are not formed over the first and second semiconductor fins (30A, 30B), the first raised active region 32A can contact the entirety of sidewall surfaces and the top surface of the first semiconductor fin 30A, and the second raised active region 32B can contact the entirety of sidewall surfaces and the top surface of the second semiconductor fin 30B.

The first semiconductor fin 30A and elements contacting the first semiconductor fin 30A and located over the insulator layer 20 can collectively constitute a first electrode (30A, 32A, 34, 40, 42, 48, 56). Likewise, the second semiconductor fin 30B and elements contacting the second semiconductor fin 30B and located over the insulator layer 20 collectively constitute a second electrode (30B, 32B, 34, 40, 42, 48, 56). In each electrode, a gate stack (40, 42, 48, 56) and an additional raised active region 34 may, or may not, be present.

In one embodiment, the semiconductor fins (30A, 30B, 30C) can be single crystalline, and the various raised active regions (32A, 32B, 34, 36) can be formed as single crystalline doped semiconductor material portions in epitaxial alignment with the single crystalline structure of underlying semiconductor fins (30A, 30B, 30C). In this case, the various raised active regions (32A, 32B, 34, 36) can be formed with crystallographic facets. In one embodiment, the crystallographic orientations of the first and second semiconductor fins (30A, 30B) can be selected such that ridges at which two adjoining crystallographic facets are adjoined to one another runs parallel to each other between the first and second semiconductor fins (30A, 30B). For example, a ridge of the first raised active region 32A and a ridge of the second raised active region 32B can be parallel to each other, and can be laterally spaced from each other by a spacing that is invariant under lateral translation along the lengthwise direction of the first and second semiconductor fins (30A, 30B). The invariant spacing is herein referred to as a width w of a nanochannel. The width w can be in a range from 0.5 nm to 100 nm. As used herein, a nanochannel refers to a gap having a uniform width that is invariant under lateral translation and has a dimension less than 100 nm.

Thus, a pair of parallel electrodes is formed on a substrate (10, 20). Each of the pair of parallel electrodes includes at least a semiconductor fin (30A or 30B), and a nanochannel is formed between the pair of parallel electrodes. In one embodiment, the pair of parallel electrodes can include a first electrode (30A, 32A, 34, 40, 42, 48, 56) and a second electrode (30B, 32B, 34, 40, 42, 48, 56).

Figure 4A:
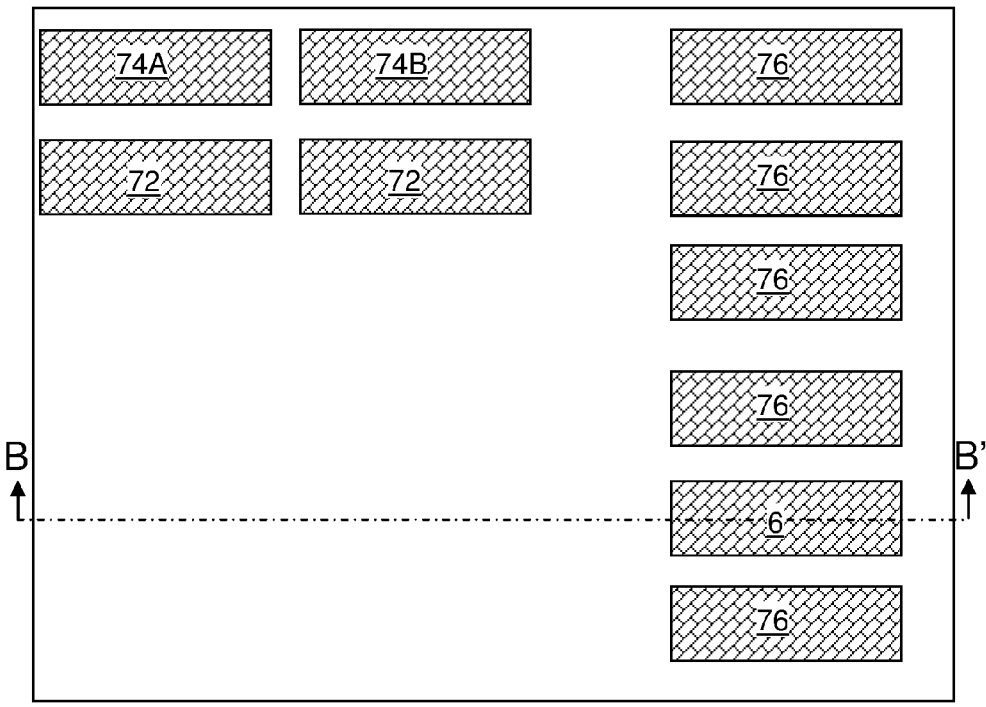
FIG. 4A is a top-down view of the first exemplary structure after formation of a metal interconnect structure according to the first embodiment of the present disclosure.
Figure 4B:
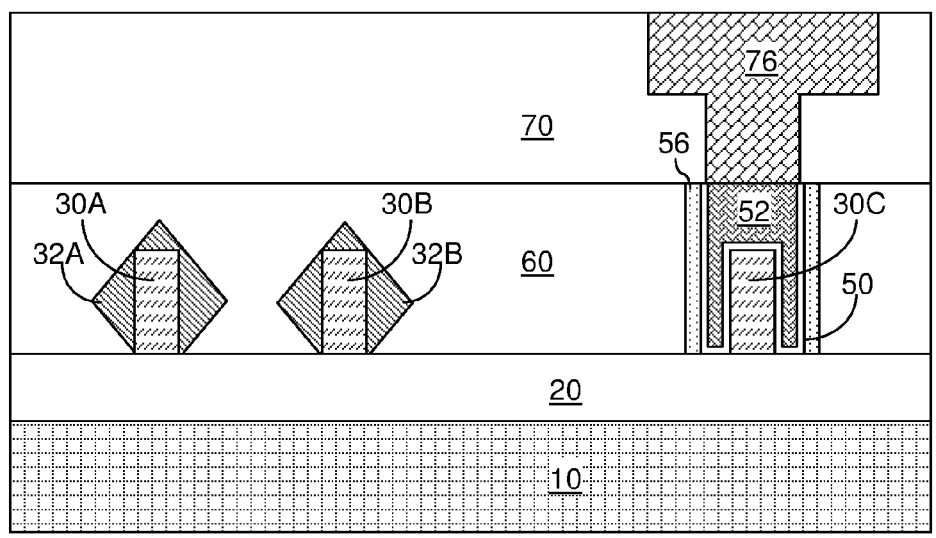
FIG. 4B is a vertical cross-sectional view of the first exemplary structure along the vertical plane B-B' of FIG. 4A.

Referring to FIGS. 4A and 4B, a planarization dielectric layer 60 can be formed over the gate structures (40, 42, 48, 56) and planarized, for example, by chemical mechanical planarization. Optionally, each stack of a dielectric gate cap 48, a gate electrode 42, and a gate dielectric 40 can be replaced with a permanent gate structure (50, 52) that includes a replacement gate dielectric 50 and a replacement gate electrode 52.

At least one metal interconnect structure-containing layer (70, 72, 74A, 74B, 76) can be formed over the planarization dielectric layer 60. The at least one metal interconnect structure-containing layer 70 includes conductive structures (72, 74A, 74B, 76) embedded in at least one dielectric material layer 70. The conductive structures (72, 74A, 74B, 76) can include a first conductive structure 74A that is electrically shorted to the first electrode (30A, 32A, 34, 40, 42, 48, 56), e.g., by physically contacting the additional raised active region 34 (See FIG. 3A) located on the first semiconductor fin 30A, and further include a second conductive structure 74B that is electrically shorted to the second electrode (30B, 32B, 34, 40, 42, 48, 56), e.g., by contacting the additional raised active region 34 (See FIG. 3A) located on the second semiconductor fin 30B. Thus, each of the first and second conductive structures (74A, 74B) is electrically shorted to one of the pair of parallel electrodes (30A, 32A, 30B, 32B, 34, 40, 42, 48, 56). The conductive structures (72, 74A, 74B, 76) can further include gate contact conductive structures 72 that contact the gate electrodes 52 straddling the first or second semiconductor fins (30A, 30B). Further, the conductive structures (72, 74A, 74B, 76) can include device contact conductive structures 76, which provide electrical contact to various components of semiconductor devices formed employing the device semiconductor fins 30C. For example, the device contact conductive structures 76 can be electrically shorted to a source region, a drain region, or a gate of a fin field effect transistor. The conductive structures (72, 74A, 74B, 76) can include metal lines and/or metal vias as known in the art. In one embodiment, the conductive structures (72, 74A, 74B, 76) can be placed such that a region overlying the first and second raised active regions (32A, 32B) do not include any conductive structure (72, 74A, 74B, 76).

Figure 5A:
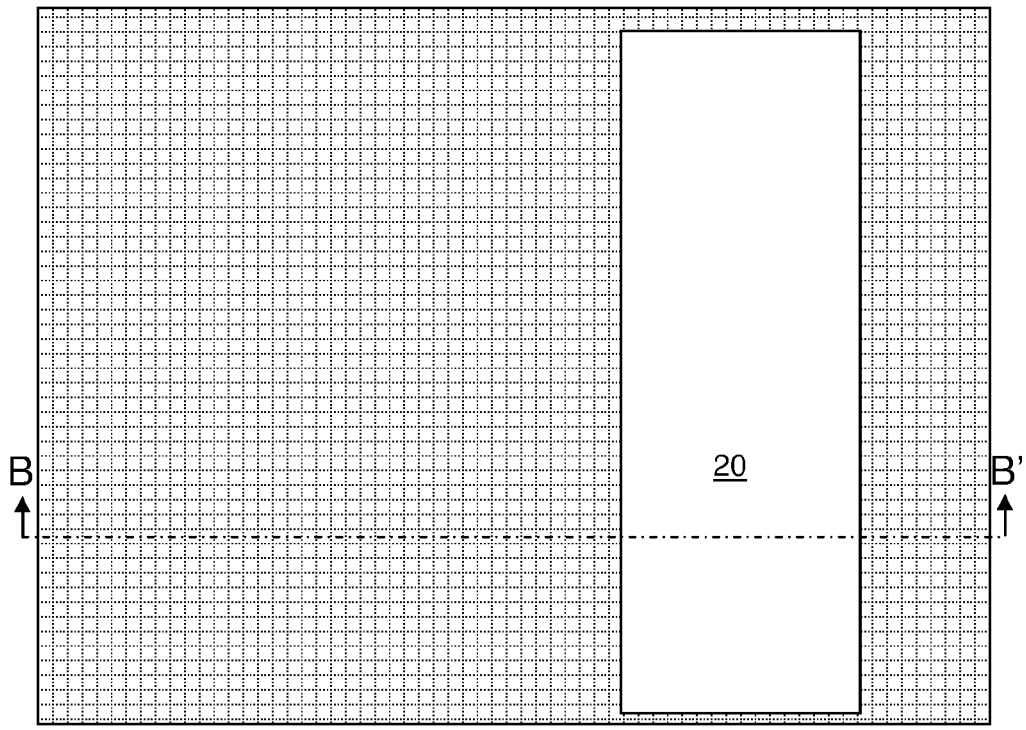
FIG. 5A is a top-down view of the first exemplary structure after forming a cavity in a handle substrate according to the first embodiment of the present disclosure.
Figure 5B:
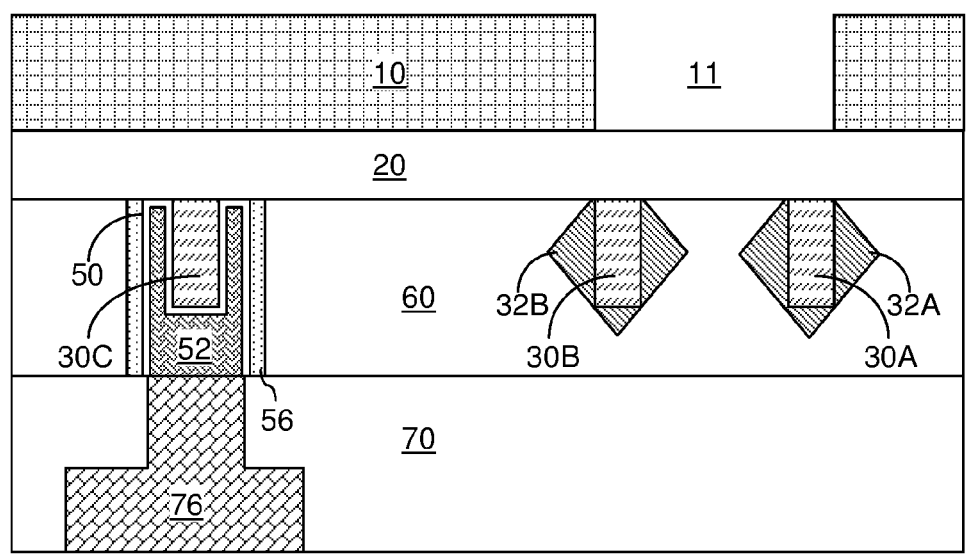
FIG. 5B is a vertical cross-sectional view of the first exemplary structure along the vertical plane B-B' of FIG. 5A.

Referring to FIGS. 5A and 5B, the handle substrate 10 can be thinned to a thickness in the range from 30 μm to 100 μm, for example, by grinding, polishing, or other mechanical and/or chemical means for thinning a substrate. Subsequently, the first exemplary structure can be flipped upside down so that the physically exposed horizontal surface of the handle substrate 10 is positioned at the top. A photoresist layer (not shown) can be applied over the physically exposed surface of the handle substrate 10, and can be lithographically patterned to form an opening in a region overlying the gap between the first semiconductor fin 30A and the second semiconductor gap 30B. The pattern in the photoresist layer can be transferred through the handle substrate 10 by an etch, which can be an isotropic etch or an anisotropic etch. In one embodiment, the etch can be selective to the dielectric material of the insulator layer 20. A cavity that replicates the shape of the photoresist layer can be formed within the handle substrate 10, which is herein referred to as a handle substrate cavity 11.

Figure 6A:
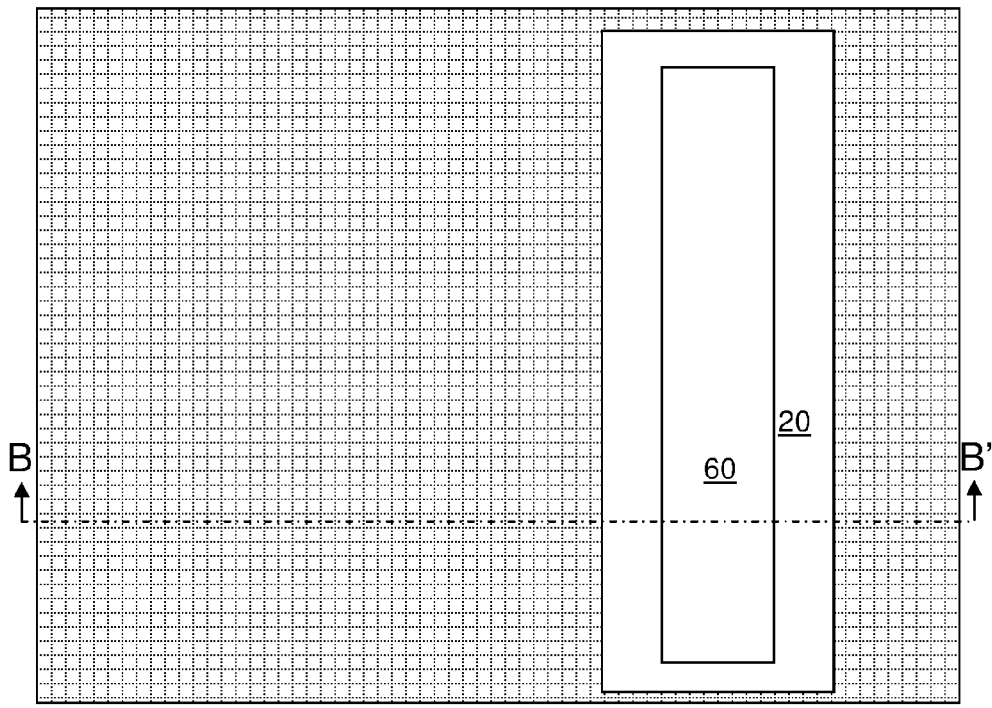
FIG. 6A is a top-down view of the first exemplary structure after formation of a cavity through an insulator layer according to the first embodiment of the present disclosure.
Figure 6B:
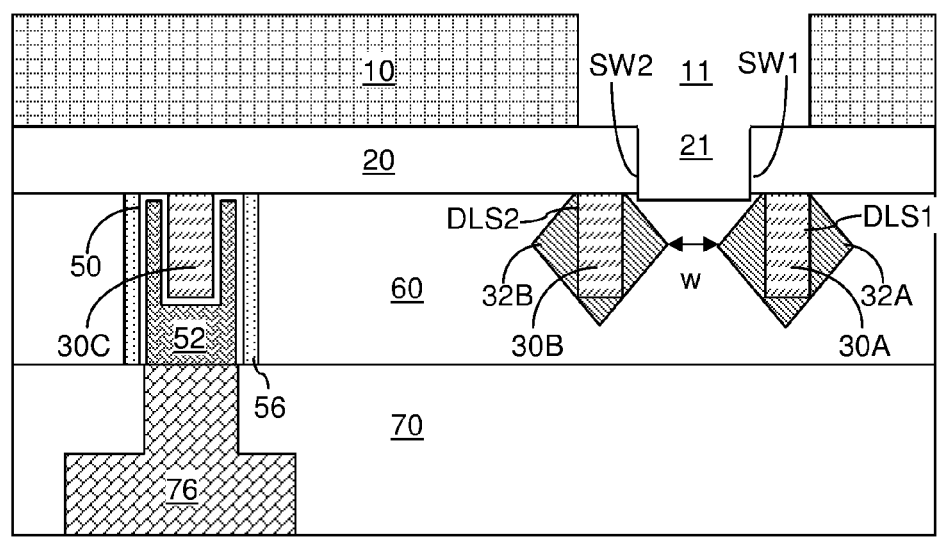
FIG. 6B is a vertical cross-sectional view of the first exemplary structure along the vertical plane B-B' of FIG. 6A.

Referring to FIGS. 6A and 6B, a cavity is formed through the insulator layer 20, which is herein referred to as an insulator cavity 21. The insulator cavity 21 and the handle substrate cavity 11 collectively constitute a contiguous cavity in the substrate (10, 20). In one embodiment, the photoresist layer employed to pattern the handle substrate cavity 11 can be removed, and a new photoresist layer may be applied and patterned to serve as the template for a pattern transfer into the insulator layer, for example, by an isotropic etch or an anisotropic etch. In this case, the new photoresist layer can be subsequently removed, for example, by ashing. Alternately, the photoresist layer may be removed, and a permanent spacer or a disposable spacer can be formed on the sidewalls of the handle substrate 10 around the handle substrate cavity 11, and can be employed as the template for a pattern transfer into the insulator layer, for example, by an isotropic etch or an anisotropic etch. Yet alternately, the photoresist layer and/or the handle substrate 10 can be employed as a template for a pattern transfer into the insulator layer, for example, by an isotropic etch or an anisotropic etch. In this case, the handle substrate cavity 11 and the insulator cavity 21 can have vertically coincident sidewalls. As used herein, two surfaces are "vertically coincident" if there exists a vertical plane that includes the two surfaces. Other methods of forming a cavity in a substrate can also be employed to form a contiguous cavity (11, 21) that includes the handle substrate cavity 11 and the insulator cavity 21.

The locations of the sidewalls of the insulator cavity 21 are selected such the cavity through the insulator layer 20 does not extend outside of the region defined by a pair of distal lengthwise sidewalls (DSL1, DSL2) of the first and second semiconductor fins (30A, 30B). In one embodiment, the locations of the sidewalls of the insulator cavity 21 are selected such that a first sidewall of the insulator cavity is positioned within an area defined by a first distal lengthwise sidewall of the first semiconductor fin 30A and the ridge of the first raised active region 32A that defines the width w, while a second sidewall SW2 of the insulator cavity 21 is positioned within an area defined by a second distal lengthwise sidewall DLS2 of the second semiconductor fin 30B and the ridge of the second raised active region 32B that defines the width w.

Figure 7A:
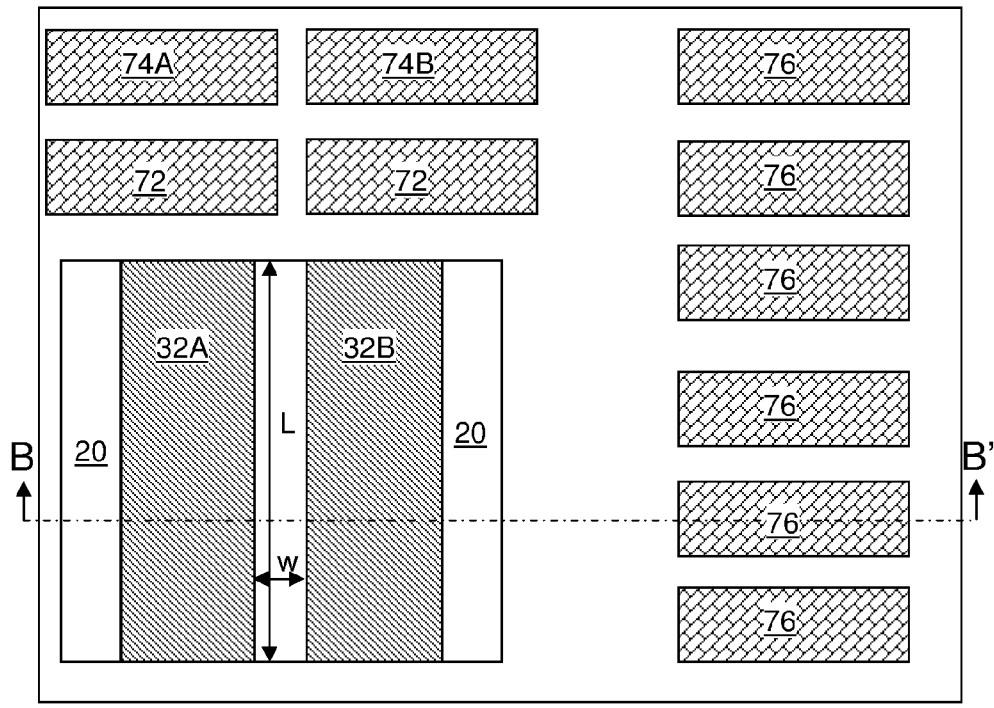
FIG. 7A is a top-down view of the first exemplary structure after formation of a cavity through the metal interconnect structure according to the first embodiment of the present disclosure.
Figure 7B:
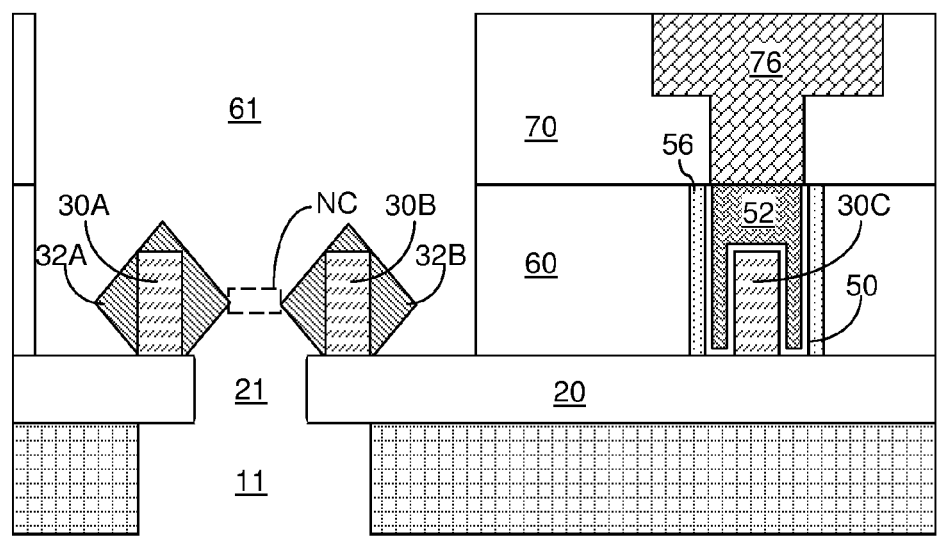
FIG. 7B is a vertical cross-sectional view of the first exemplary structure along the vertical plane B-B' of FIG. 7A.

Referring to FIGS. 7A and 7B, the first exemplary structure can be flipped upside down again. A cavity, which is herein referred to as a dielectric layer cavity 61, is formed though the at least one dielectric material layer 70 and the planarization dielectric layer 60. The dielectric layer cavity 61 can be formed so that the area of the dielectric layer cavity 61 overlap with the area of the insulator cavity 20 within an area defined by a portion of the nanochannel having the width w and laterally bounded by the first raised active region 32A and the second raised active region 32B. The dielectric layer cavity 61 can be formed by etching a region of the at least one dielectric material layer 70 over the pair of parallel electrodes (30A, 30B, 32A, 32B, 50, 52, 56, 34) such that sidewalls of the dielectric layer cavity 61 vertically extend from a topmost surface of the contiguous cavity (11, 21, 61) to a horizontal surface of the substrate (10, 20) and surfaces of the pair of parallel electrodes (30A, 30B, 32A, 32B, 50, 52, 56, 34), and specifically, surfaces of the first and second raised active regions (30A, 30B). The etching can be performed, for example, by an anisotropic etch employing a temporary etch mask such as a patterned photoresist layer. The sidewalls of the dielectric layer cavity 61 may, or may not, be vertical.

The overlap between the nanochannel bounded by the first raised active region 32A and the second raised active region 32B and the area of the dielectric layer cavity 61 defines a nanochannel NC. The nanochannel NC is defined by a parallel pair of proximal ridges of the first raised active region 30A and the second raised active region 30B that are separated by the width w and a pair of vertical sidewalls of the dielectric layer cavity 61 that are spaced from each other by a length L. In one embodiment, the nanochannel NC can have a rectangular cross-sectional shape in which a pair of sides has the dimension of the width w and another pair of sides has the dimension of the length L. The width w can be in a range from 0.5 nm to 100 nm, and the length L can be in a range from 2 nm to 10,000 nm.

The set of the handle substrate cavity 11, the insulator cavity 21, and the dielectric layer cavity 61 collectively constitute a contiguous cavity (11, 21, 61). The least cross-sectional area along contiguous paths from the top of the contiguous cavity (11, 21, 61) and the bottom of the contiguous cavity (11, 21, 61) occurs at the nanochannel having the width w and the length L. The contiguous cavity (11, 21, 61) passes through the substrate (10, 20) and the metal interconnect structure-containing layer (70, 72, 74A, 74B, 76) and includes the nanochannel NC.

In one embodiment, the nanochannel NC can have a rectangular periphery having the width w in a range from 0.5 nm to 100 nm, and the length L that is greater than the width. The width w can be perpendicular to the lengthwise direction of the semiconductor fins (30A, 30B) and the length can be parallel to the lengthwise direction of the semiconductor fins (30A, 30B). Each of the pair of parallel electrodes (30A, 30B, 32A, 32B, 50, 52, 56, 34) can include a raised active region (32A or 32B) including a doped semiconductor material. The nanochannel NC can have a periphery including edges of the raised active regions (32A, 32B). The periphery of the nanochannel NC can further include two portions of sidewalls of the at least one dielectric material layer located within the metal interconnect structure-containing layer (70, 72, 74A, 74B, 76). The sidewalls can be surfaces defining a lateral extent of the contiguous cavity (11, 21, 61), and specifically, defining the length L of the dielectric layer cavity 61 portion of the contiguous cavity (11, 21, 61).

Figure 8A:
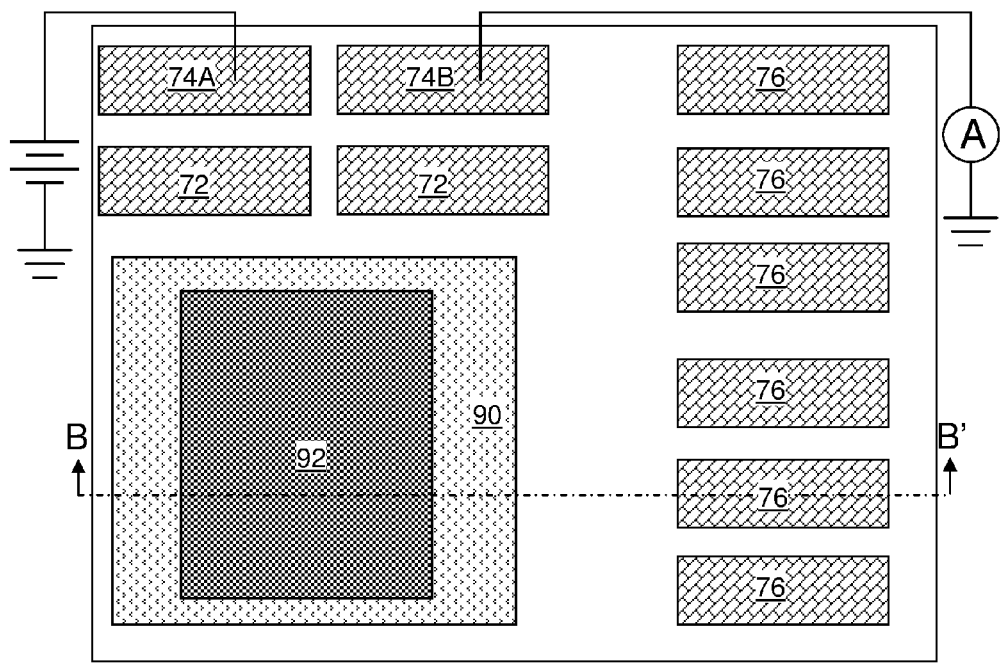
FIG. 8A is a top-down view of the first exemplary structure after application of a gel, a nanoscale string, and external electrodes according to the first embodiment of the present disclosure.
Figure 8B:
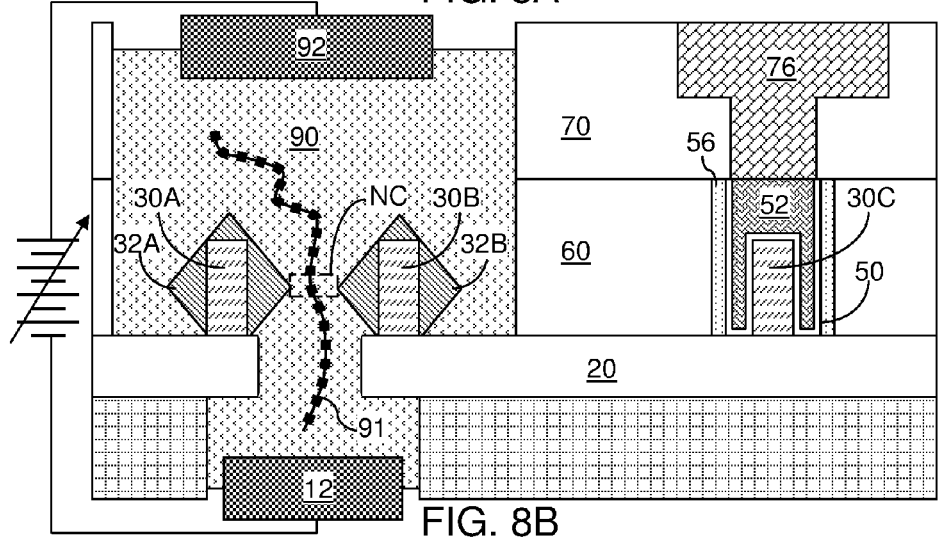
FIG. 8B is a vertical cross-sectional view of the first exemplary structure along the vertical plane B-B' of FIG. 8A.

Referring to FIGS. 8A and 8B, a medium 90 can be applied in the contiguous cavity (11, 21, 61). As used herein, a "medium" or a "material transport medium" refers to a material through which transport of an embedded material is possible. In one embodiment, the medium 90 can be an electrophoresis gel as known in the art. In another embodiment, the medium 90 can be a solution in which molecules or other materials can be transported. In this case, the solution can be an aqueous solution. The medium 90 can include at least one nanoscale string 91. The medium 90 can be disposed within the contiguous cavity (11, 21, 61) and optionally above or below the first exemplary structure. As used herein, a "nanoscale string" refers to an elongated structure extending predominantly along one direction and having dimensions that are less than 100 nm along directions perpendicular to the local lengthwise direction of the elongated structure. The local lengthwise direction of a nanoscale string can gradually change so that twists and turns in the global structure of the nanoscale string are possible. Typical examples of a nanoscale string include DNA strands and carbon nanotubes.

External electrodes (92, 12) can be disposed across the nanochannel NC. A first external electrode 92 can be disposed above the top surface of the substrate (10, 20) and on the medium 90, and the second external electrode 12 can be disposed below the top surface of the substrate (10, 20) and on the medium 90. For example, a first external electrode 92 can be disposed over the nanochannel NC and within the portion of the medium 90 overlying the nanochannel NC, and a second external electrode 12 can be disposed under the nanochannel NC and within the portion of the medium 90 underlying the nanochannel NC. It is understood that the first exemplary structure may be oriented in any convenient orientation to facilitate positioning of the first and second external electrodes (92, 12).

Subsequently, the first external electrode 92 and the second external electrode 12 can be electrically biased with respect to each other to induce flow of electrically charged material in the medium 90 and through the nanochannel NC. A leakage current measurement circuitry can be connected to the first conductive structure 74A and the second conductive structure 74B to enable measurement of the change in the leakage current through the nanochannel NC as a nanoscale string passes through the nanochannel NC. The leakage current measurement circuitry can be configured to measure the leakage current through the pair of parallel electrodes (30A, 30B, 32A, 32B, 50, 52, 34) and a portion of the electrically charged material within the nanochannel NC, which can be a nanoscale string passing through the nanochannel NC due to the electrical bias voltage applied across the first external electrode 92 and the second external electrode 12.

In the first exemplary structure, a pair of parallel electrodes (30A, 30B, 32A, 32B, 50, 52, 34) is located on a substrate (10, 20). Each of the pair of parallel electrodes (30A, 30B, 32A, 32B, 50, 52, 34) includes at least a semiconductor fin (30A or 30B), and a nanochannel NC is present between the pair of parallel electrodes (30A, 30B, 32A, 32B, 50, 52, 34). A metal interconnect structure-containing layer (70, 72, 74A, 74B, 76) is present over the substrate (10, 20). Conductive structures (72, 74A, 74B, 76) are embedded in at least one dielectric material layer 70. The conductive structures (72, 74A, 74B, 76) includes a first conductive structure 74A that is electrically shorted to the first electrode (30A, 32A, 50, 52, 34) among the pair of parallel electrodes, and further includes a second conductive structure 74B that is electrically shorted to the second electrode (30B, 32B, 50, 52, 34) among the pair of parallel electrodes.

With the medium 90 and the electrical connections illustrated in FIGS. 8A and 8B, the first exemplary structure is an electrophoresis system that enables leakage current measurement as the nanoscale string 91 passes through the nanochannel NC.

Figure 9A:
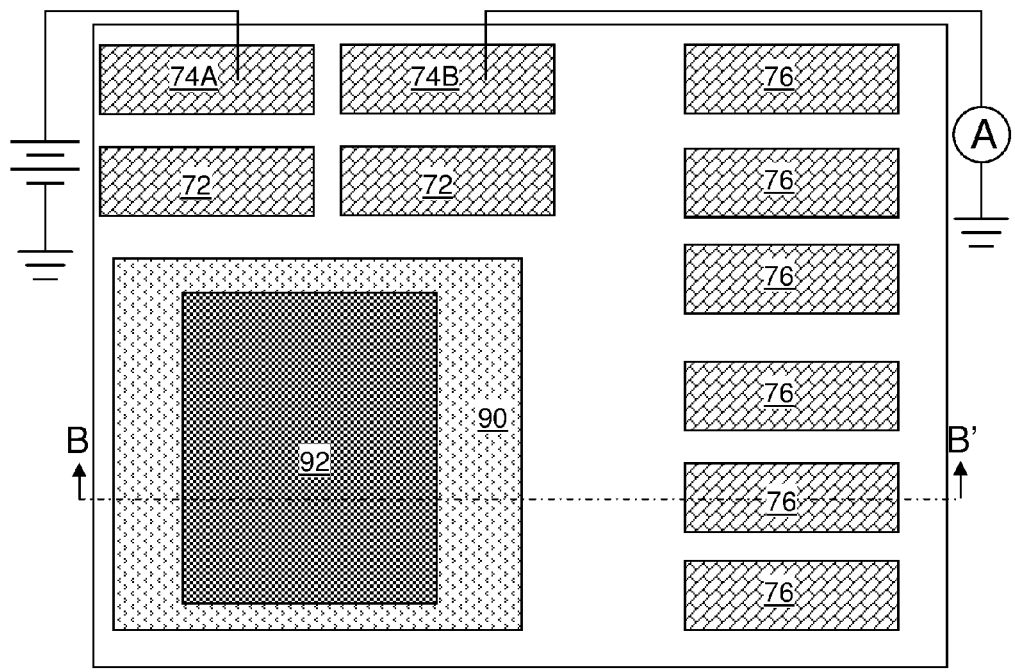
FIG. 9A is a top-down view of a first variation of the first exemplary structure after according to the first embodiment of the present disclosure.
Figure 9B:
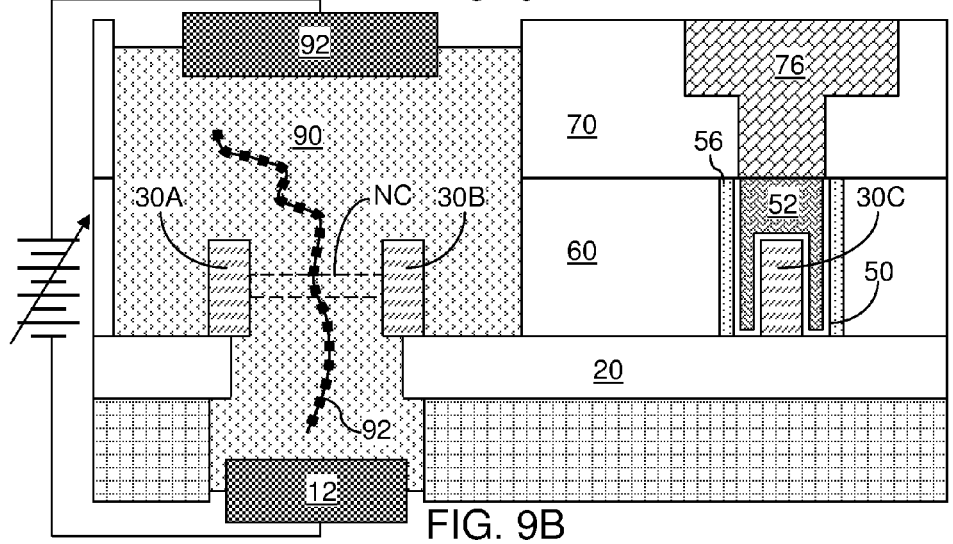
FIG. 9B is a vertical cross-sectional view of the first variation of the first exemplary structure along the vertical plane B-B' of FIG. 9A.

Referring to FIGS. 9A and 9B, a first variation of the first exemplary structure can be derived from the first exemplary structure by omitting formation of the various raised active regions (32A, 332B, 34, 36) at the processing steps of FIGS. 3A and 3B, i.e., by skipping the selective deposition process that forms the various raised active regions (32A, 332B, 34, 36) of the first exemplary structure. In this case, the width of the nanochannel can be the same as the lateral distance between a proximal pair of lengthwise sidewalls of the first and second semiconductor fins (30A, 30B), i.e., the lateral distance between the lengthwise sidewall of the first semiconductor fin 30A that is proximal to the second semiconductor fin 30B and the lengthwise sidewall of the second semiconductor fin 30B that is proximal to the first semiconductor fin 30A.

Figure 10A:
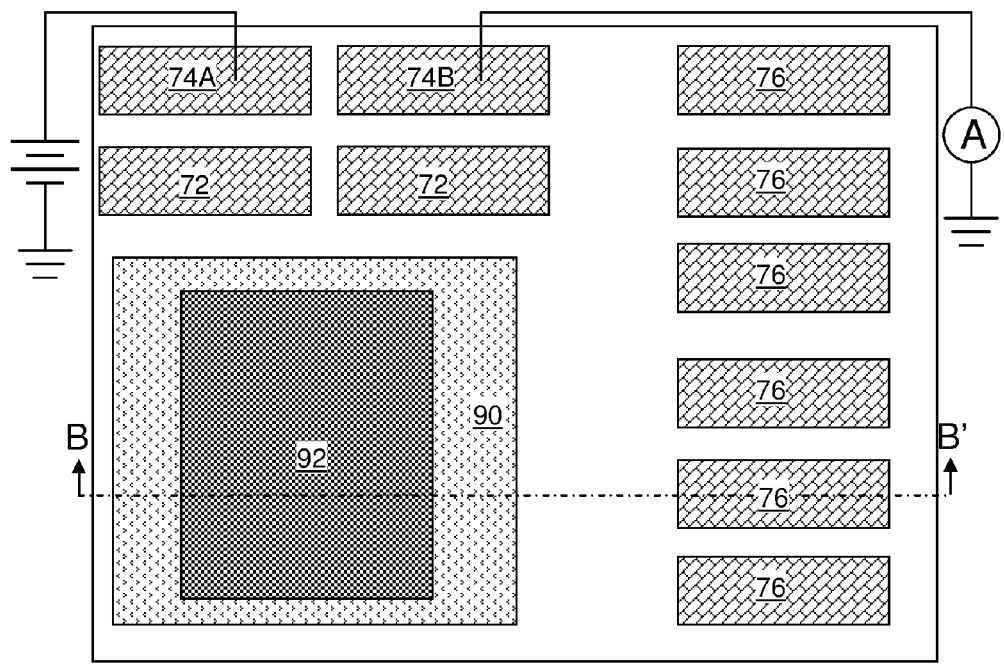
FIG. 10A is a top-down view of a second variation of the first exemplary structure according to the first embodiment of the present disclosure.
Figure 10B:
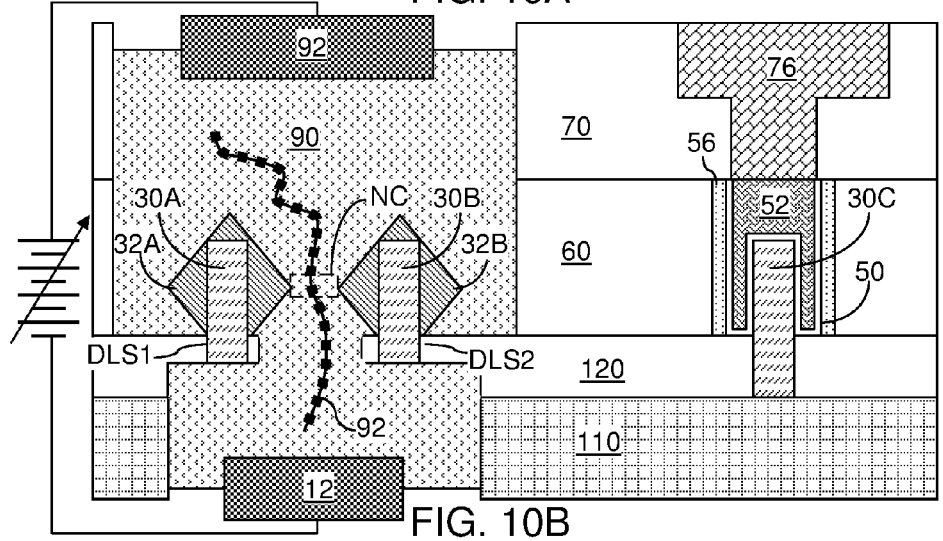
FIG. 10B is a vertical cross-sectional view of the second variation of the first exemplary structure along the vertical plane B-B' of FIG. 10A.

Referring FIGS. 10A and 10B, a second variation of the first exemplary structure can be derived from the first exemplary structure or the first variation of the first exemplary structure by employing a bulk semiconductor substrate in lieu of an SOI substrate. In this case, semiconductor fins (30A, 30B, 30C) can be formed by patterning an upper portion of the bulk semiconductor substrate as originally provided, and the unpatterned portions of the bulk semiconductor substrate constitutes a semiconductor substrate 110. A shallow trench isolation layer 120 can be deposited over the top surface of the semiconductor substrate 110 such that the shallow trench isolation layer 120 laterally surrounds lower portions of each semiconductor fin (30A, 30B, 30C). The processing steps of FIGS. 2A, 2B, 3A, 3B, 4A, 4B, 5A, and 5B can be subsequently performed. Optionally, the processing steps of FIGS. 3A and 3B can be omitted.

The semiconductor substrate 110 can be thinned, and a cavity can be formed through the semiconductor substrate 110. In one embodiment, during formation of a cavity through the semiconductor substrate 110, an overetch into the shallow trench isolation layer 120 may cause sidewalls within the semiconductor substrate 110 to be vertically coincident with sidewalls within the shallow trench isolation layer 120. High selectivity of the etch process to the material of the shallow trench isolation layer during formation of the cavity in the semiconductor substrate 110 can reduce or remove the etching into the shallow trench isolation layer.

Another cavity, which is herein referred to as an insulator cavity, is formed through the shallow trench isolation layer 120. The locations of the sidewalls of the insulator cavity are selected such the insulator cavity through the shallow trench isolation layer 120 does not extend outside of the region defined by a pair of distal lengthwise sidewalls (DLS1, DLS2) of the first and second semiconductor fins (30A, 30B). Subsequently, the processing steps of FIGS. 7A, 7B, 8A, and 8B can be performed to provide the second variation of the first exemplary structure.

Figure 11A:
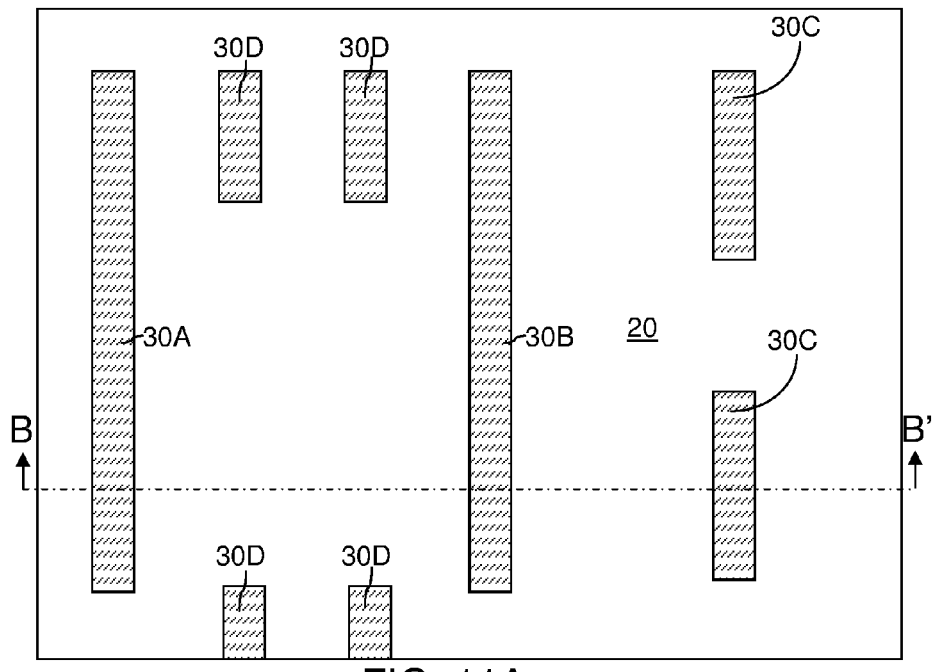
FIG. 11A is a top-down view of a second exemplary structure after formation of semiconductor fins according to a second embodiment of the present disclosure.
Figure 11B:
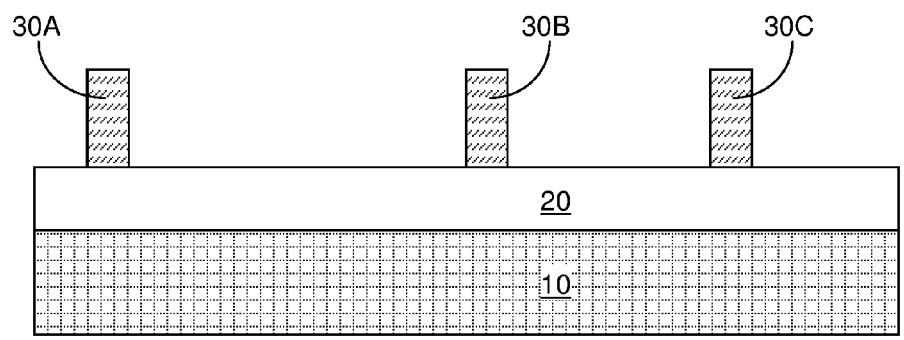
FIG. 11B is a vertical cross-sectional view of the second exemplary structure along the vertical plane B-B' of FIG. 11A.

Referring to FIGS. 11A and 11B, a second exemplary structure according to a second embodiment of the present disclosure is formed by modifying the layout of the semiconductor fins (30A, 30B, 30C, 30D) from the layout illustrated in FIG. 1A. Specifically, at least one additional semiconductor fin 30D is formed between the first semiconductor fin 30A and the second semiconductor fin 30B. In one embodiment, at least one pair of additional semiconductor fins 30D can be formed between the first semiconductor fin 30A and the second semiconductor fin 30B such that there exist a sufficient gap between the first and second semiconductor fins (30A, 30B) that is not filled with selectively deposited semiconductor material in a subsequent selective deposition of a second semiconductor material.

Figure 12A:
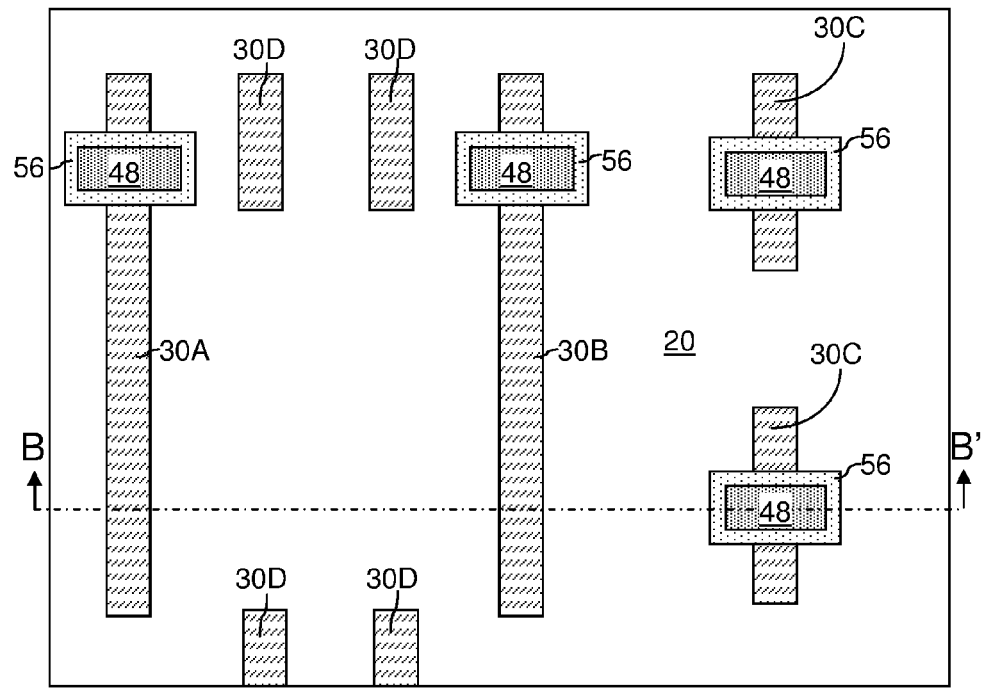
FIG. 12A is a top-down view of the second exemplary structure after formation of gate structures according to the second embodiment of the present disclosure.
Figure 12B:
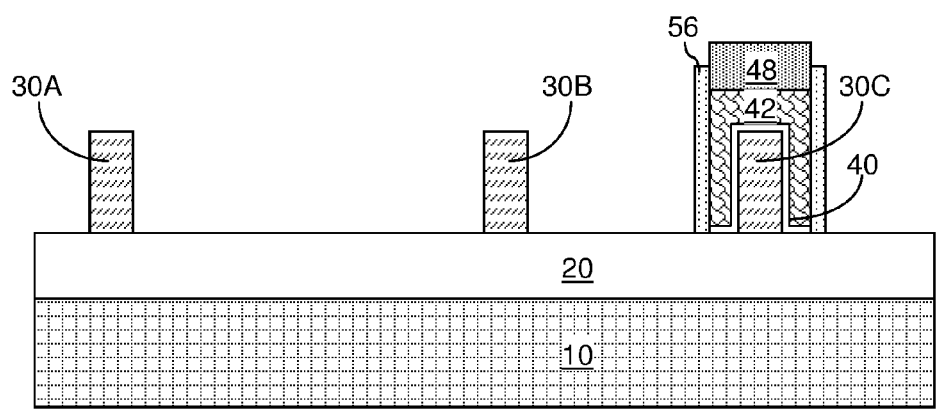
FIG. 12B is a vertical cross-sectional view of the second exemplary structure along the vertical plane B-B' of FIG. 12A.

Referring FIGS. 12A and 12B, gate structures (40, 42, 48, 56) can be formed employing the same methods as in the first embodiment. The gate structures (40, 42, 48, 56) may, or may not, be formed on the first and/or second semiconductor fins (30A, 30B), and may, or may not, be formed on the additional semiconductor fins 30D. If the gate structures (40, 42, 48, 56) are not formed across the first and second semiconductor fins (30A, 30B), the entirety of each of the first and second semiconductor fins (30A, 30B) can be doped with dopants of the same conductivity type, which can be p-type or n-type, so that the entirety of each semiconductor fin (30A, 30B) is a conductive structure.

Figure 13A:
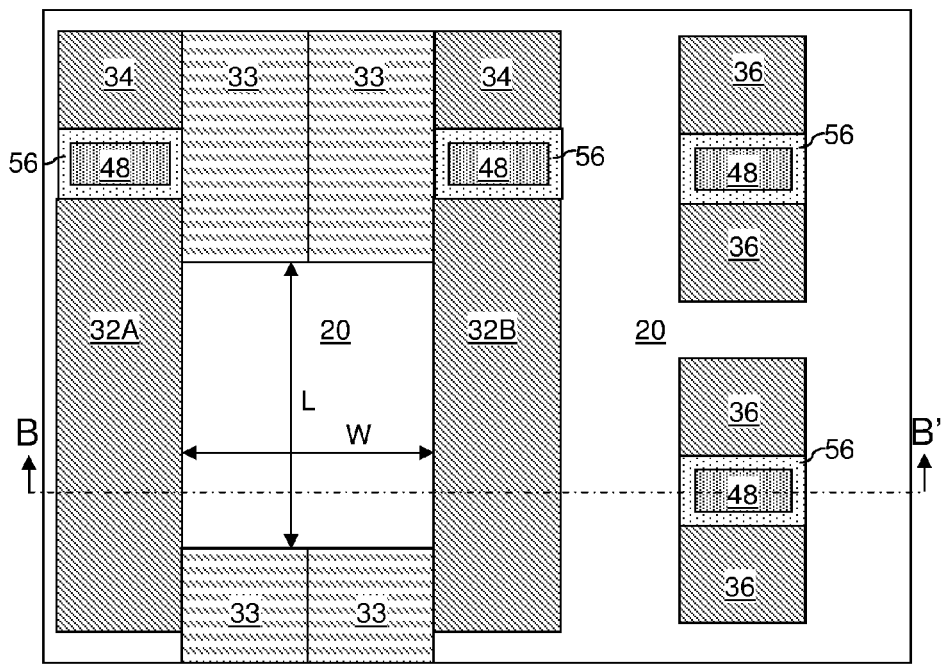
FIG. 13A is a top-down view of the second exemplary structure after formation of raised active regions and raised inactive regions according to the second embodiment of the present disclosure.
Figure 13B:
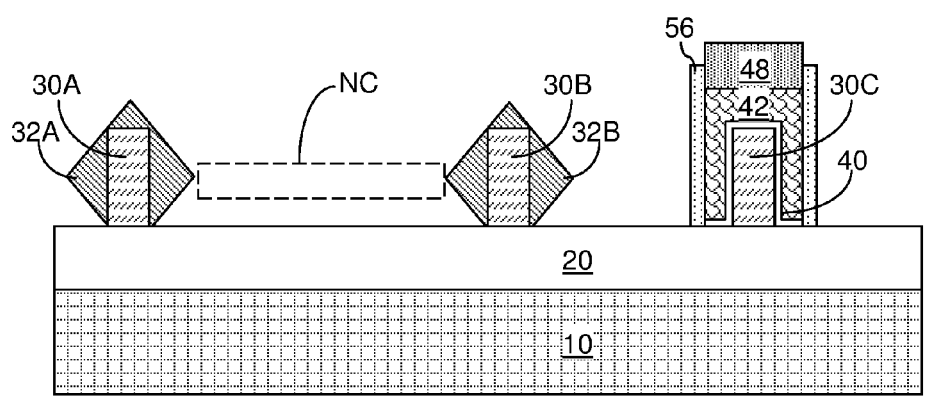
FIG. 13B is a vertical cross-sectional view of the second exemplary structure along the vertical plane B-B' of FIG. 13A.

Referring to FIGS. 13A and 13B, a selective deposition process can be optionally performed to form various raised semiconductor regions. A subset of the various semiconductor regions can be subsequently doped to form various raised active regions (32A, 32B, 34, 36). Another subset of the various semiconductor regions can remain undoped, and constitute raised inactive regions 34, which are semiconductor regions that are not doped. As used herein, an "inactive region" refers to an undoped semiconductor material portion, which can be substantially intrinsic and have high enough resistivity (>$1.0\times10^3$ Ohm-cm) to be treated as an insulator. As used herein, a "raised inactive region" refers to an undoped semiconductor material portion that is formed on a surface of a semiconductor fin. The selective deposition process deposits a semiconductor material, which is herein referred to as a second semiconductor material, on semiconductor surfaces while preventing deposition of the second semiconductor material on dielectric surfaces. The selective deposition process can be the same as in the first embodiment provided that in-situ doping is not employed in the second embodiment.

In one embodiment, the selective deposition process can be a selective epitaxy process that deposits the second semiconductor material. The second semiconductor material can be any semiconductor material that can be deposited as a single crystalline material or a polycrystalline material. The second semiconductor material may be the same as, or may be different from, the first semiconductor material. In one embodiment, the second semiconductor material can be single crystalline, in which can the second semiconductor material in the various raised active regions (32A, 32B, 34, 36) can be epitaxially aligned to the semiconductor fins (30A, 30B, 30C). Various portions of the semiconductor fins (30A, 30B, 30C) may be doped suitably prior to, or after, the selective deposition process. For example, fin source regions (not shown) and fin drain regions (not shown) can be formed in various portions of the semiconductor fins (30A, 30B, 30C) by ion implantation and/or diffusion from the raised active regions (32A, 32B, 34, 36) and/or by other methods known in the art.

The selective deposition process may deposit the second semiconductor material as an intrinsic semiconductor material. In one embodiment, portions of semiconductor fins (30A, 30B, 30C) that underlie gate structures (40, 42, 48, 56) can constitute body regions of field effect transistors.

The raised active regions (32A, 32B, 34, 36) include a first raised active region 32A formed on at least a portion of the first semiconductor fin 30A, and a second raised active region 32B formed on at least a portion of the second semiconductor fin 30B. At least one additional raised active region 34 can be formed on the first and/or second semiconductor fins (30A, 30B) if at least one gate structure (40, 42, 48, 56) is present on the first and/or second semiconductor fins (30A, 30B). Device raised active regions 36, i.e., raised active regions that are employed as an element of a semiconductor device as known in the art, can be formed on device semiconductor fins 30C. In an embodiment in which gate structures (40, 42, 48, 56) are not formed over the first and second semiconductor fins (30A, 30B), the first raised active region 32A can contact the entirety of sidewall surfaces and the top surface of the first semiconductor fin 30A, and the second raised active region 32B can contact the entirety of sidewall surfaces and the top surface of the second semiconductor fin 30B.

The first semiconductor fin 30A and elements contacting the first semiconductor fin 30A and located over the insulator layer 20 can collectively constitute a first electrode (30A, 32A, 34, 40, 42, 48, 56). Likewise, the second semiconductor fin 30B and elements contacting the second semiconductor fin 30B and located over the insulator layer 20 collectively constitute a second electrode (30B, 32B, 34, 40, 42, 48, 56). In each electrode, a gate stack (40, 42, 48, 56) and an additional raised active region 34 may, or may not, be present.

In one embodiment, the semiconductor fins (30A, 30B, 30C) can be single crystalline, and the various raised active regions (32A, 32B, 34, 36) can be formed as single crystalline doped semiconductor material portions in epitaxial alignment with the single crystalline structure of underlying semiconductor fins (30A, 30B, 30C). In this case, the various raised active regions (32A, 32B, 34, 36) can be formed with crystallographic facets. In one embodiment, the crystallographic orientations of the first and second semiconductor fins (30A, 30B) can be selected such that ridges at which two adjoining crystallographic facets are adjoined to one another runs parallel to each other between the first and second semiconductor fins (30A, 30B). For example, a ridge of the first raised active region 32A and a ridge of the second raised active region 32B can be parallel to each other, and can be laterally spaced from each other by a spacing that is invariant under lateral translation along the lengthwise direction of the first and second semiconductor fins (30A, 30B). The invariant spacing is herein referred to as a width w of a nanochannel. The width w can be in a range from 10 nm to 1,000 nm. As used herein, a nanochannel refers to a gap having a uniform width that is invariant under lateral translation and has a dimension less than 100 nm.

Thus, a pair of parallel electrodes is formed on a substrate (10, 20). Each of the pair of parallel electrodes includes at least a semiconductor fin (30A or 30B), and a nanochannel is formed between the pair of parallel electrodes. In one embodiment, the pair of parallel electrodes can include a first electrode (30A, 32A, 34, 40, 42, 48, 56) and a second electrode (30B, 32B, 34, 40, 42, 48, 56).

Raised inactive regions 33 can be formed on the additional semiconductor fins 30D. The raised inactive regions 33 include undoped semiconductor material. The raised inactive regions 33 can be formed by performing the selective deposition process and preventing implantation of electrical dopants into the semiconductor material portions deposited directly on the additional semiconductor fins 30D, while implanting p-type dopants and/or n-type dopants to form the various raised active regions (32A, 32B, 34, 36). The lateral distances between neighboring semiconductor fins (30A, 30B, 30C, 30D) are selected such that the raised inactive regions 33 adjoin the first raised active region 32A and the second raised active regions 32B. A rectangular opening defined by inner peripheries of the first and second raised active regions (32A, 32B) and the raised inactive regions 33 can be formed over the substrate (10, 20). In one embodiment, the opening can have a width w that is invariant along the lengthwise direction of the first and second semiconductor fins (30A, 30B) and a length L that is invariant along the horizontal direction that is perpendicular to the lengthwise direction of the first and second semiconductor fins (30A, 30B).

Figure 14A:
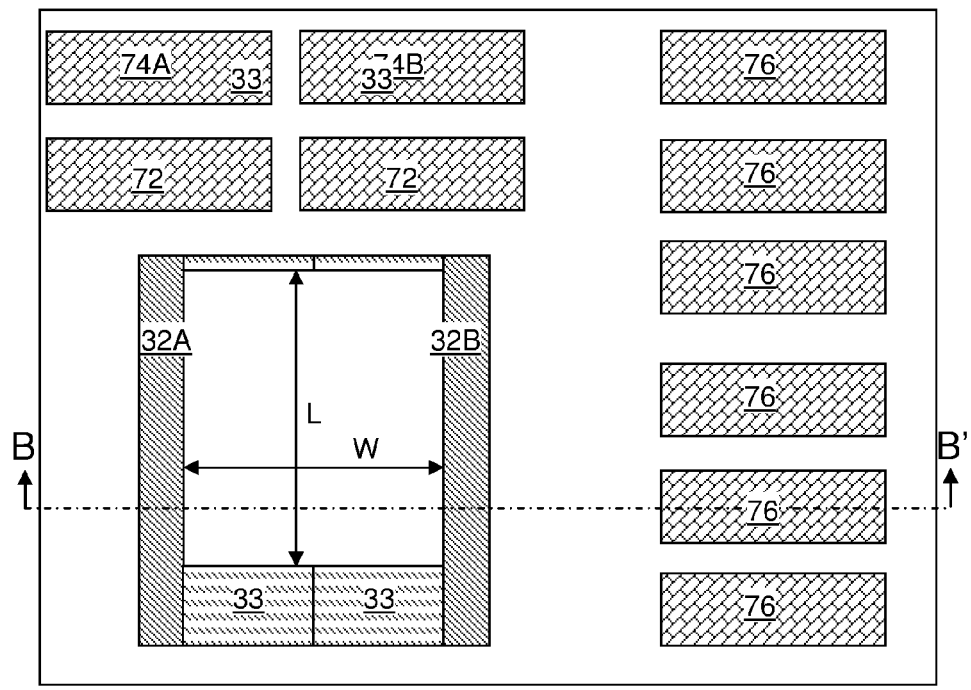
FIG. 14A is a top-down view of the second exemplary structure after formation of cavities through the handle substrate, the insulator layer, and a metal interconnect structure according to the second embodiment of the present disclosure.
Figure 14B:
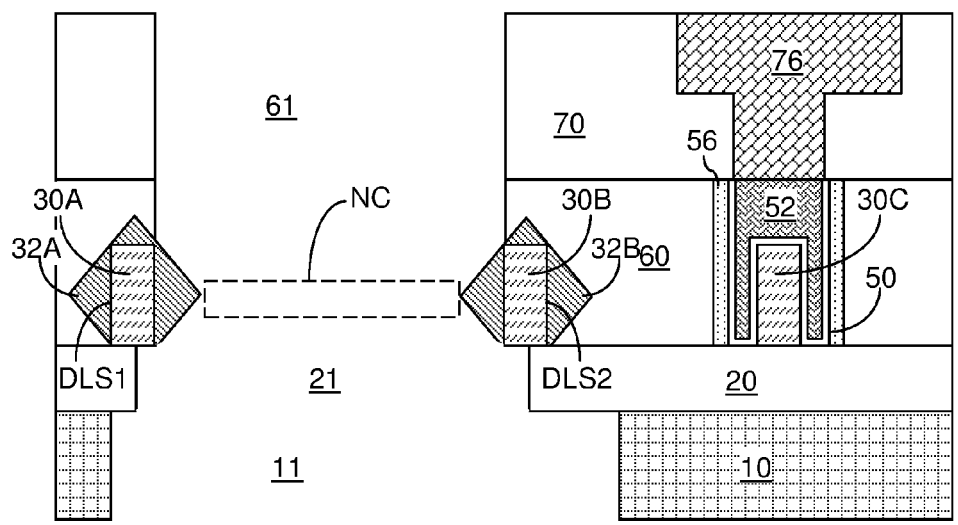
FIG. 14B is a vertical cross-sectional view of the second exemplary structure along the vertical plane B-B' of FIG. 14A.

Referring to FIGS. 14A and 14B, the processing steps of FIGS. 4A, 4B, 5A, 5B, 6A, 6B, 7A, and 7B can be subsequently performed. A contiguous cavity (11, 21, 61)

can be formed in the same manner as in the first embodiment. The nanochannel NC can be defined by a rectangular periphery having a width w in a range from 30 nm to 100 nm, and a length L that is greater than the width w. In one embodiment, the length L can be in a range from 100 nm to 10,000 nm. The locations of the sidewalls of the insulator cavity 21 can be selected such the cavity through the insulator layer 20 does not extend outside of the region defined by a pair of distal lengthwise sidewalls (DSL1, DSL2) of the first and second semiconductor fins (30A, 30B).

Figure 15A:
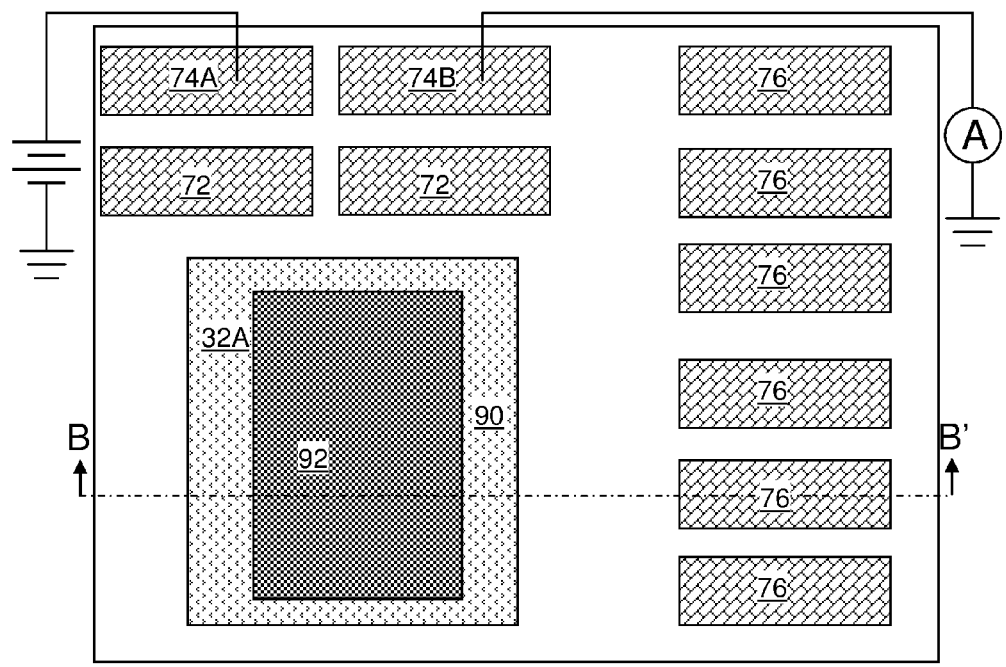
FIG. 15A is a top-down view of the second exemplary structure after application of a gel, a nanoscale string, and external electrodes according to the second embodiment of the present disclosure.
Figure 15B:
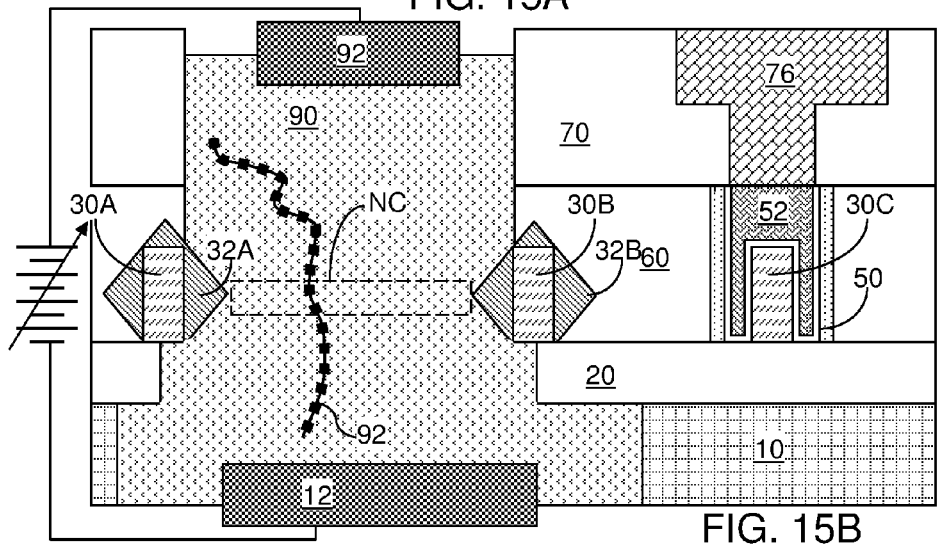
FIG. 15B is a vertical cross-sectional view of the second exemplary structure along the vertical plane B-B' of FIG. 8A.

Referring to FIGS. 15A and 15B, the processing steps of FIGS. 8A and 8B can be performed. In one embodiment, the second exemplary structure of FIGS. 15A and 15B can be an electrophoresis system or a solution-based material transport system, and may be operated in the same manner as in the first embodiment illustrated in FIGS. 8A, 8B, 9A, 9B, 10A, and 10B.

Figure 16A:
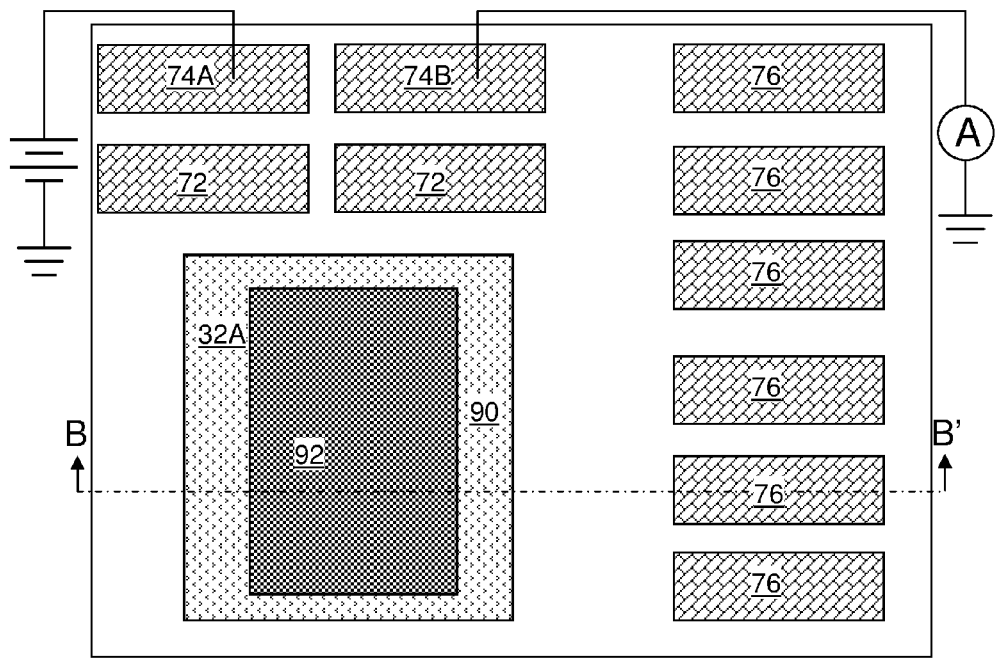
FIG. 16A is a top-down view of a first variation of the second exemplary structure after according to the second embodiment of the present disclosure.
Figure 16B:
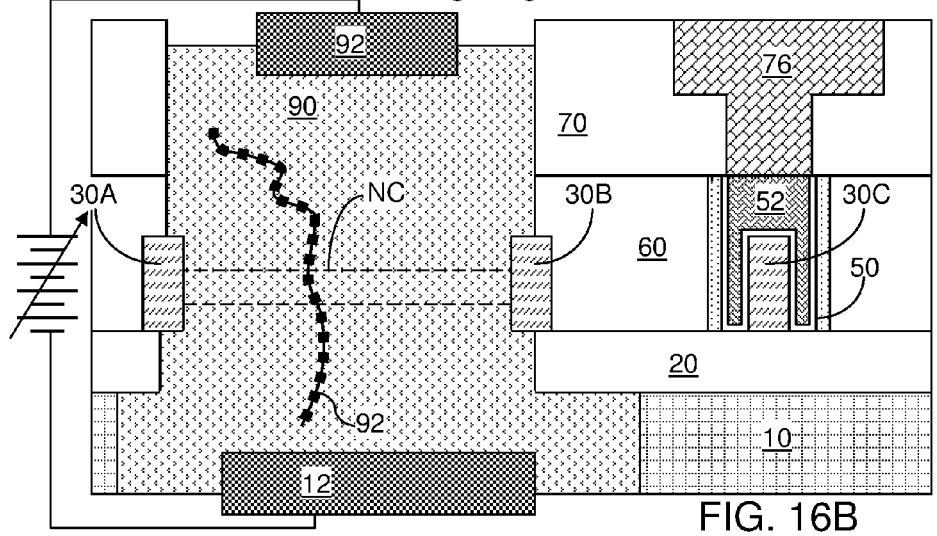
FIG. 16B is a vertical cross-sectional view of the first variation of the second exemplary structure along the vertical plane B-B' of FIG. 16A.

Referring to FIGS. 16A and 16B, a first variation of the second exemplary structure can be derived from the second exemplary structure by omitting the selective deposition process illustrated in FIGS. 13A and 13B. In this case, the length L of the nanochannel NC can be defined by the dimensions of the cavity through the at least one dielectric material layer 70 along the lengthwise direction of the first and second semiconductor fins (30A, 30B) that are parallel to each other. The width w of the nanochannel NC can be defined by the distance between a pair of proximal lengthwise sidewalls of the first semiconductor fins 30A and the second semiconductor fin 30B.

Figure 17A:
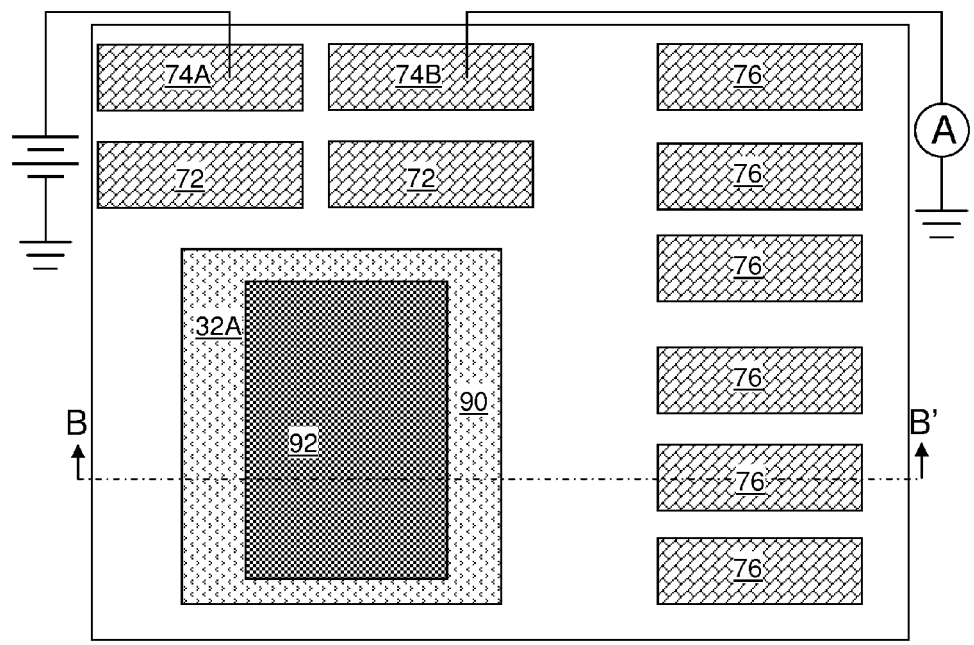
FIG. 17A is a top-down view of a second variation of the second exemplary structure according to the second embodiment of the present disclosure.
Figure 17B:
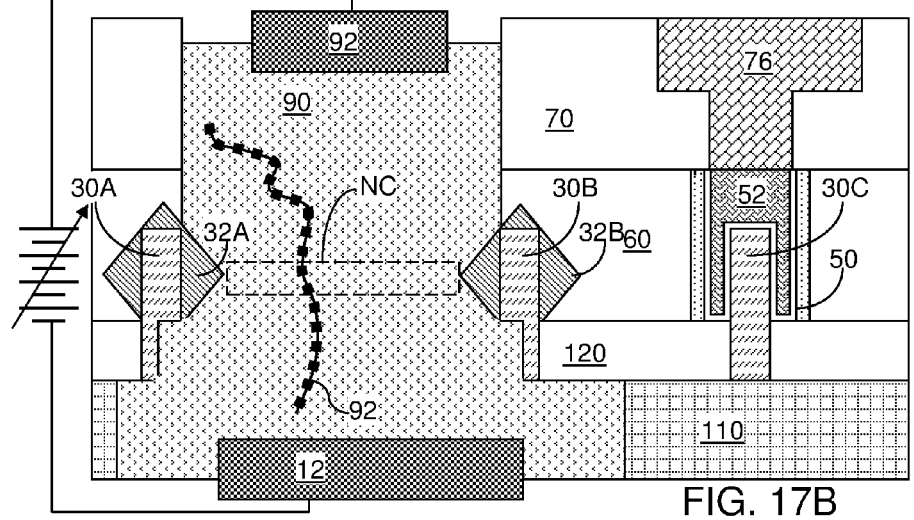
FIG. 17B is a vertical cross-sectional view of the second variation of the second exemplary structure along the vertical plane B-B' of FIG. 17A.

Referring to FIGS. 17A and 17B, a second variation of the second exemplary structure can be derived from the second exemplary structure or the first variation of the second exemplary structure by employing a bulk semiconductor substrate and employing a shallow trench isolation layer 120 in lieu of an insulator layer 20.

Figure 18A:
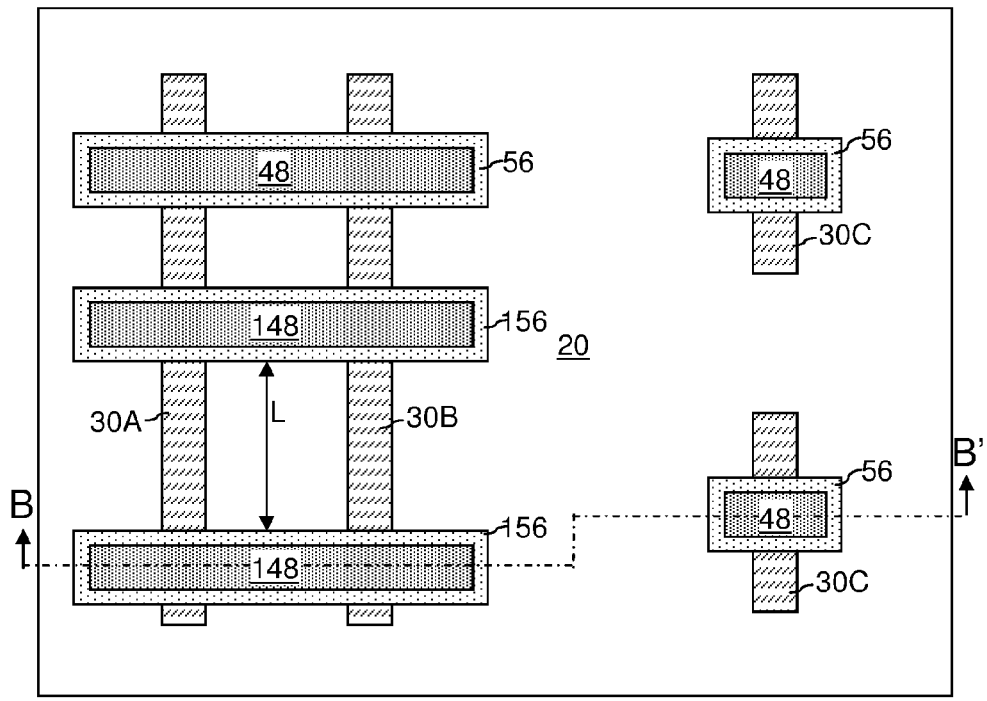
FIG. 18A is a top-down view of a third exemplary structure after formation of gate structures and dummy gate structures according to a third embodiment of the present disclosure.
Figure 18B:
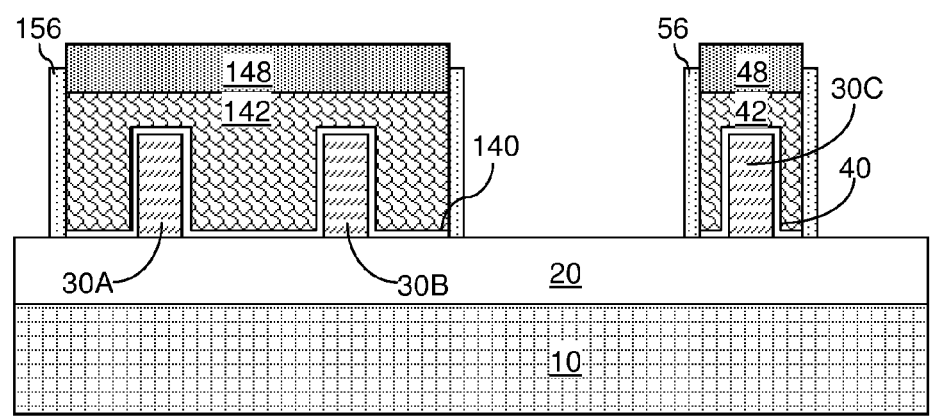
FIG. 18B is a vertical cross-sectional view of the third exemplary structure along the vertical plane B-B' of FIG. 18A.

Referring to FIGS. 18A and 18B, a third exemplary structure according to a third embodiment of the present disclosure can be derived from the first exemplary structure of FIGS. 1A and 1B by performing the processing steps of FIGS. 2A and 2B and concurrently forming at least one dummy gate structure (140, 142, 148, 156) across the first semiconductor fin 30A and the second semiconductor fin 30B. The at least one dummy gate structure (140, 142, 148, 156) can have the same stack of material layers as the gate structures (40, 42, 48, 56), and can be formed as additional patterned structures that are patterned simultaneously with formation of the gate structures (40, 42, 48, 56). If the gate structures (40, 42, 48, 56) are not formed across the first and second semiconductor fins (30A, 30B), the entirety of each of the first and second semiconductor fins (30A, 30B) can be doped with dopants of the same conductivity type, which can be p-type or n-type, so that the entirety of each semiconductor fin (30A, 30B) is a conductive structure.

In one embodiment, a pair of dummy gate structures (140, 142, 148, 156) can be positioned such that a pair of proximal sidewalls of the dummy gate structures (140, 142, 148, 156), e.g., a proximal pair of sidewalls of dummy gate spacers 156, is separated from each other by a length L, which is the length of a nanochannel to be subsequently formed. The direction of separation of the pair of proximal sidewalls of the dummy gate structures (140, 142, 148, 156) can be the lengthwise direction of the first and second semiconductor fins (30A, 30B). If a dummy gate structure (140, 142, 148, 156) does not function as a gate of a transistor, the portion of the first and/or second semiconductor fin (30A, 30B) that underlies such a dummy gate structure (140, 142, 148, 156) can be doped with p-type dopants or n-type dopants to electrically short the two portions of the semiconductor fin (30A, 30B) laterally spaced by the width of the dummy gate structure (140, 142, 148, 156).

Figure 19A:
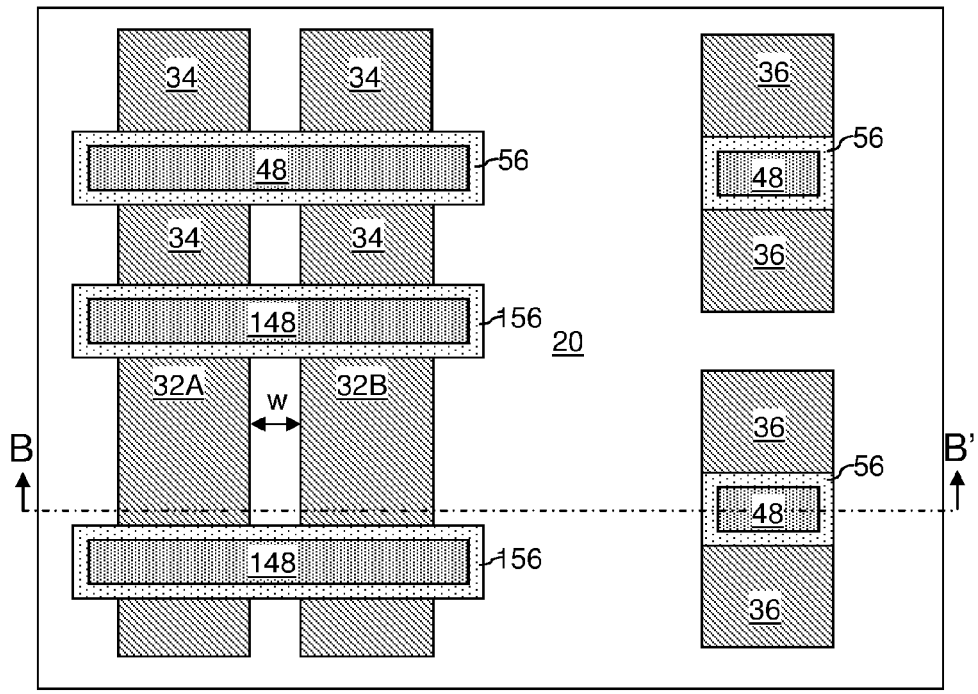
FIG. 19A is a top-down view of the third exemplary structure after formation of raised active regions according to the third embodiment of the present disclosure.
Figure 19B:
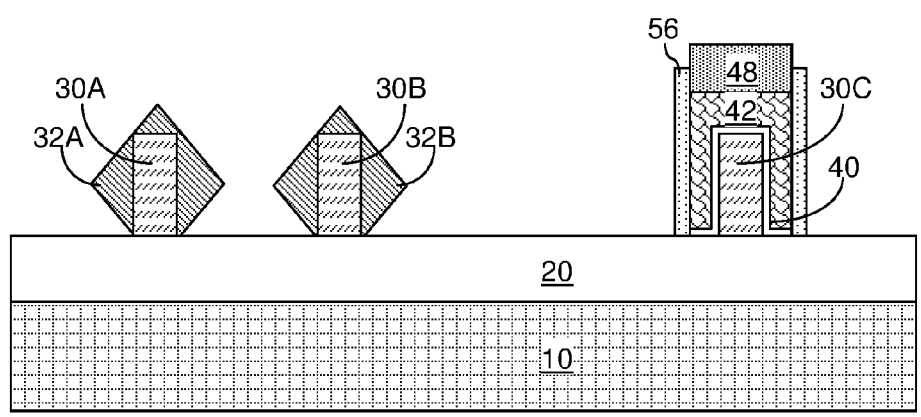
FIG. 19B is a vertical cross-sectional view of the third exemplary structure along the vertical plane B-B' of FIG. 19A.

Referring to FIGS. 19A and 19B, the processing steps of FIGS. 3A and 3B are performed to form various raised active regions (32A, 32B, 34, 36). The first raised active region 32A formed on the first semiconductor fin 30A and the second raised active region 32B formed on the second semiconductor fin 30B can be laterally spaced from each other by a width w, which is the width of a nanochannel.

Figure 20A:
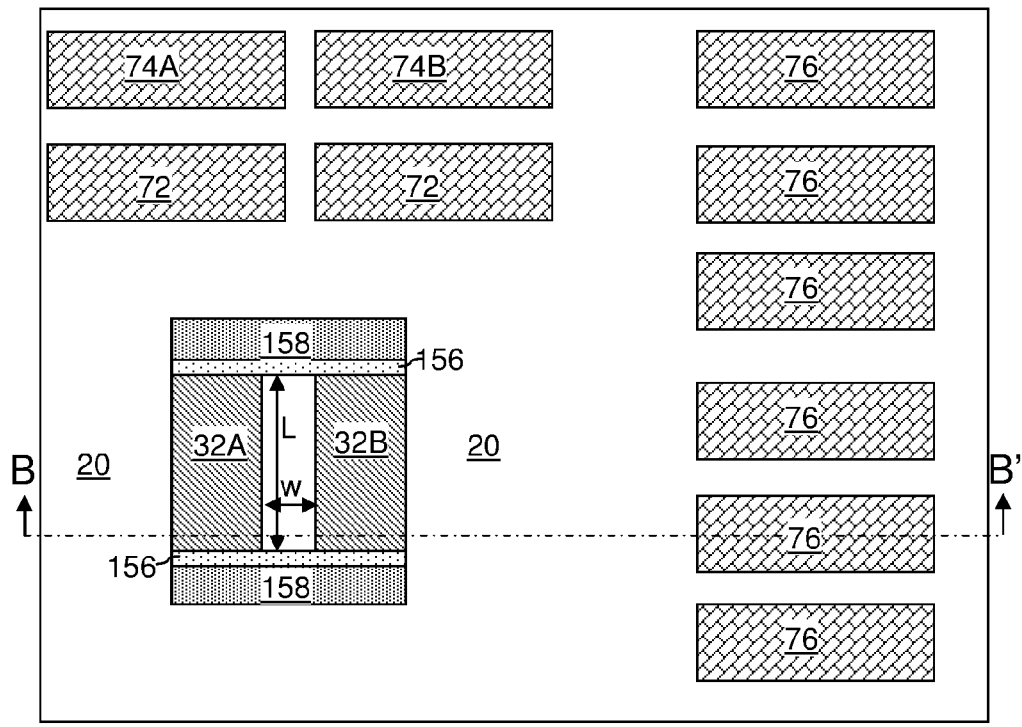
FIG. 20A is a top-down view of the third exemplary structure after formation of cavities through the handle substrate, the insulator layer, and a metal interconnect structure according to the third embodiment of the present disclosure.
Figure 20B:
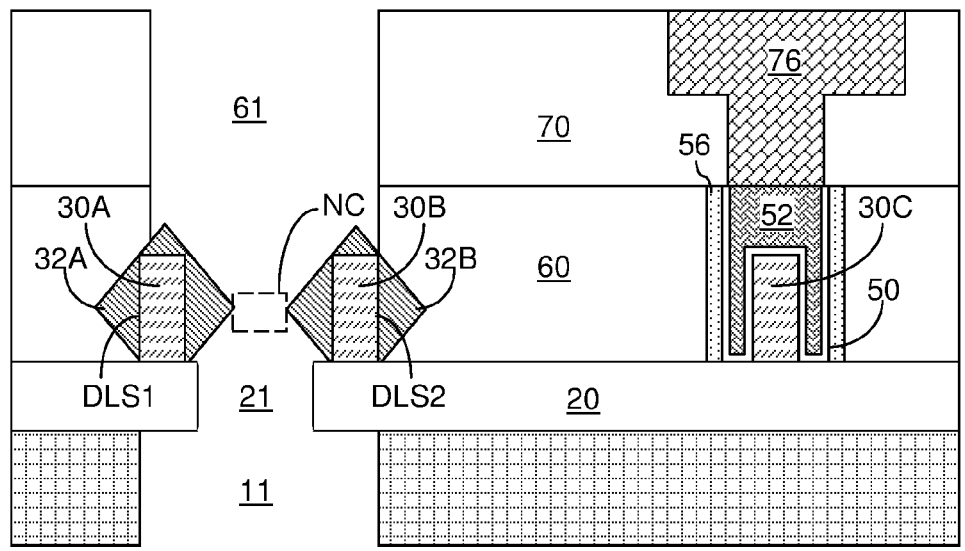
FIG. 20B is a vertical cross-sectional view of the third exemplary structure along the vertical plane B-B' of FIG. 20A.

Referring to FIGS. 20A and 20B, the processing steps of FIGS. 4A, 4B, 5A, 5B, 6A, 6B, 7A, and 7B can be subsequently performed. A contiguous cavity (11, 21, 61) can be formed in the same manner as in the first embodiment. The nanochannel NC can be defined by a rectangular periphery having a width w in a range from 0.5 nm to 100 nm, and a length L that is greater than the width w. In one embodiment, the length L can be in a range from 100 nm to 10,000 nm. The locations of the sidewalls of the insulator cavity 21 can be selected such the cavity through the insulator layer 20 does not extend outside of the region defined by a pair of distal lengthwise sidewalls (DSL1, DSL2) of the first and second semiconductor fins (30A, 30B).

If a pair of dummy gate structures (140, 142, 148, 156) is present, the length L of the nanochannel NC can be defined by the lateral spacing between the pair of proximal sidewalls of the two dummy gate structures (140, 142, 148, 156). If only a single dummy gate structure (140, 142, 148, 156) and a gate structure (40, 42, 48, 56) are present across each of the first and second semiconductor fins (30A, 30B), the length L of the nanochannel NC can be defined by the lateral spacing between the outer sidewall of the gate spacer 56 that is proximal to the dummy gate structure (140, 142, 148. 156) and the outer sidewall of the dummy gate spacer 156 that is proximal to the gate structure (40, 42, 48, 56). Thus, the length L can be defined by the spacing between a pair of dummy gate structures (140, 142, 148, 156) straddling the first and second semiconductor fins (30A, 30B), or by a pair of a dummy gate structure (140, 142, 148, 156) and a gate structure (40, 42, 48, 56).

Figure 21A:
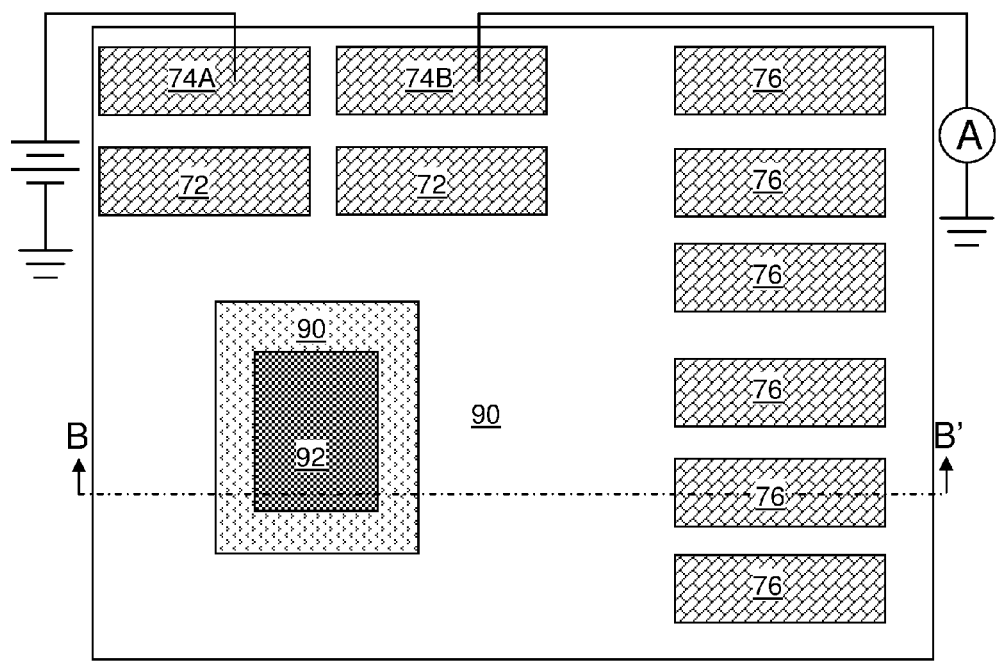
FIG. 21A is a top-down view of the third exemplary structure after application of a gel, a nanoscale string, and external electrodes according to the third embodiment of the present disclosure.
Figure 21B:
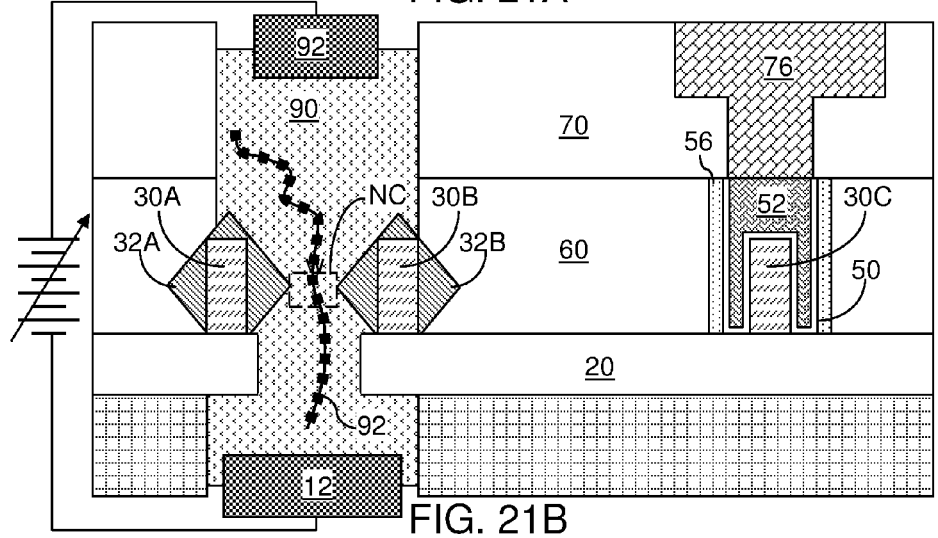
FIG. 21B is a vertical cross-sectional view of the third exemplary structure along the vertical plane B-B' of FIG. 21A.

Referring to FIGS. 21A and 21B, the processing steps of FIGS. 8A and 8B can be performed. In one embodiment, the third exemplary structure of FIGS. 21A and 21B can be an electrophoresis system or a solution-based material transport system, and may be operated in the same manner as in the first embodiment illustrated in FIGS. 8A, 8B, 9A, 9B, 10A, and 10B.

Figure 22A:
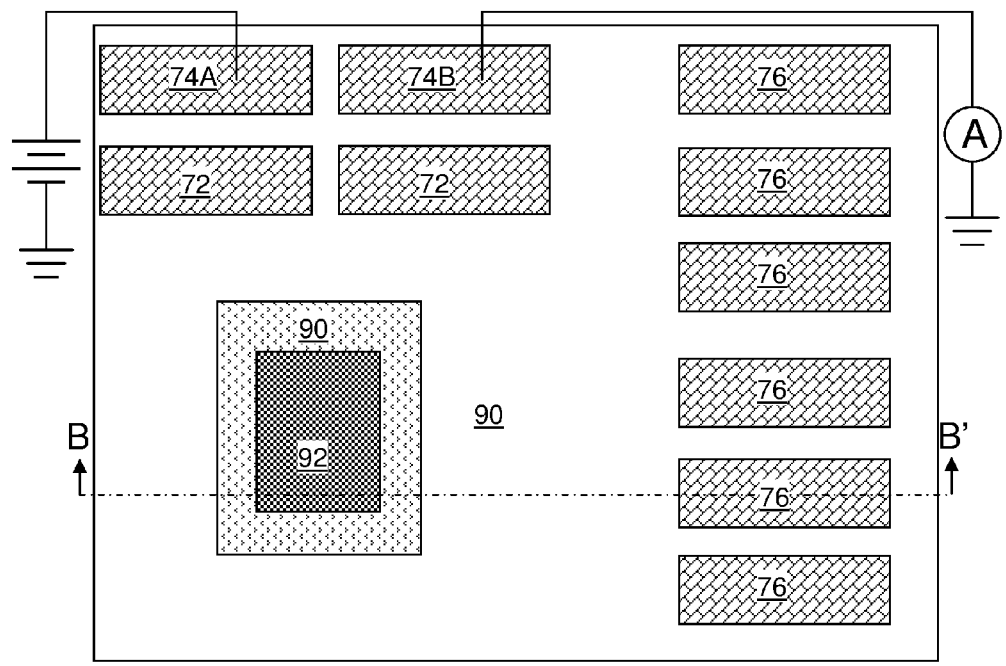
FIG. 22A is a top-down view of a first variation of the third exemplary structure after according to the third embodiment of the present disclosure.
Figure 22B:
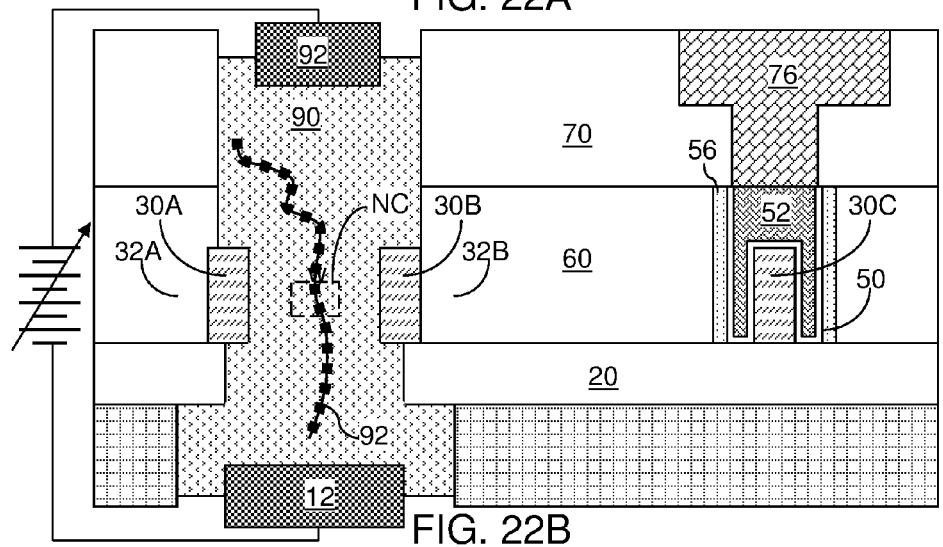
FIG. 22B is a vertical cross-sectional view of the first variation of the third exemplary structure along the vertical plane B-B' of FIG. 22A.

Referring to FIGS. 22A and 22B, a first variation of the third exemplary structure can be derived from the third exemplary structure by omitting the selective deposition process illustrated in FIGS. 19A and 19B. The width w of the nanochannel NC can be defined by the distance between a pair of proximal lengthwise sidewalls of the first semiconductor fins 30A and the second semiconductor fin 30B.

Figure 23A:
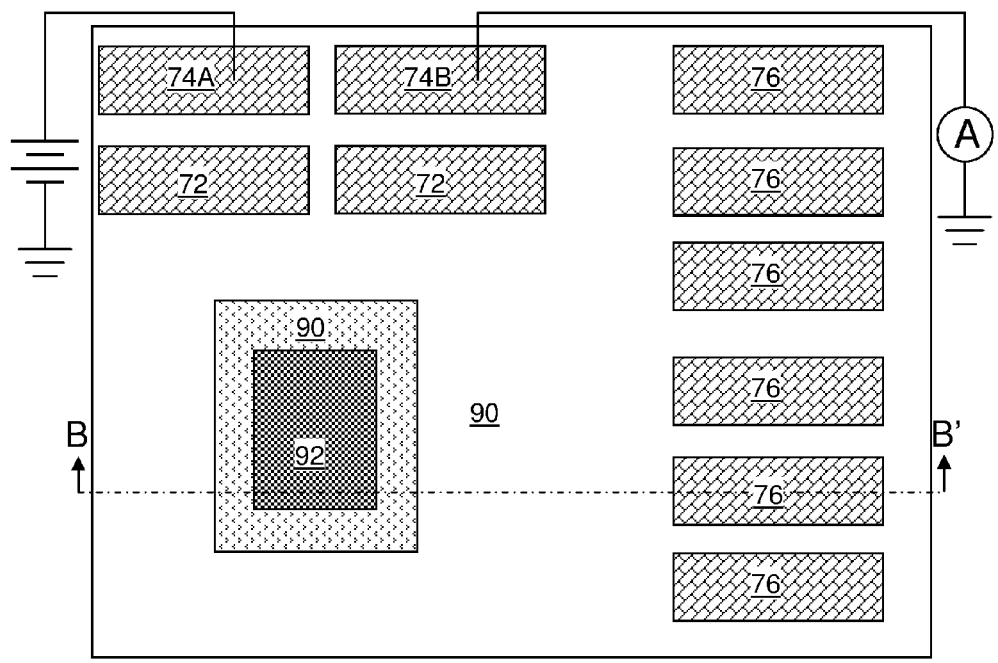
FIG. 23A is a top-down view of a second variation of the third exemplary structure according to the third embodiment of the present disclosure.
Figure 23B:
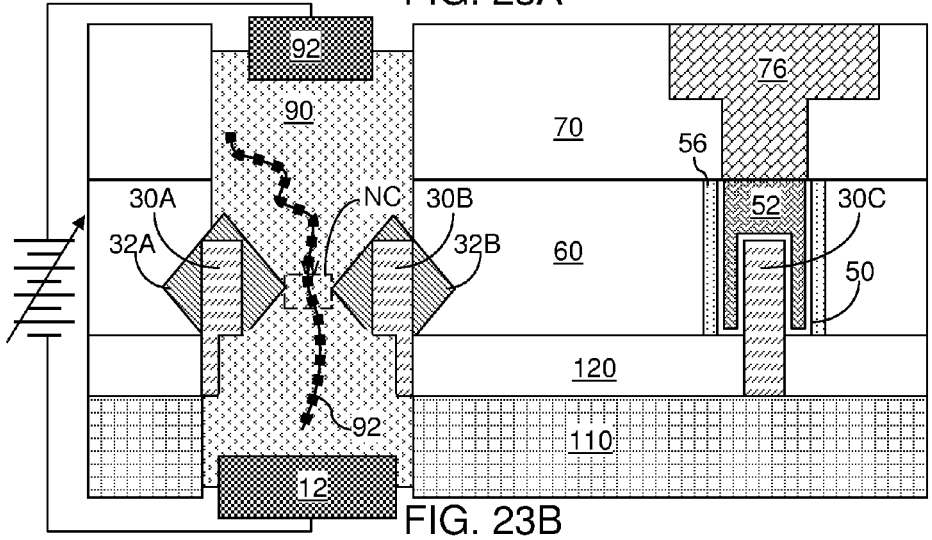
FIG. 23B is a vertical cross-sectional view of the second variation of the third exemplary structure along the vertical plane B-B' of FIG. 23A.

Referring to FIGS. 23A and 23B, a second variation of the third exemplary structure can be derived from the third exemplary structure or the first variation of the third exemplary structure by employing a bulk semiconductor substrate and employing a shallow trench isolation layer 120 in lieu of an insulator layer 20.

The various structures of the present disclosure provide a nanochannel NC, which can have a width w that can be on the order of nanometers or tens of nanometers. Further, the length L of the nanochannel NC can be selected as any dimension limited only by lithographic limitations. The various structures of the present disclosure can be employed to form a custom-tailored opening size for characterization of nanoscale strings that passes through the nanochannel during gel electrophoresis, a solution-based material transport and characterization, or by any other methods that induces movement of the nanoscale string through the nanochannel. Thus, the various structures of the present disclosure can be employed to characterize a nanoscale string such as a DNA string.

While the disclosure has been described in terms of specific embodiments, it is evident in view of the foregoing description that numerous alternatives, modifications and variations will be apparent to those skilled in the art. Each of the various embodiments of the present disclosure can be implemented alone, or in combination with any other embodiments of the present disclosure unless expressly disclosed otherwise or otherwise impossible as would be known to one of ordinary skill in the art. Accordingly, the disclosure is intended to encompass all such alternatives, modifications and variations which fall within the scope and spirit of the disclosure and the following claims.

What is claimed is:

1. A method of forming: a structure comprising:
   forming a pair of parallel electrodes on a substrate, wherein each of said pair of parallel electrodes comprises at least a semiconductor fin, wherein a nanochannel is formed between said pair of parallel electrodes;
   forming a metal interconnect structure-containing layer comprising conductive structures embedded in at least one dielectric material layer, each of said conductive structures is electrically shorted to one of said pair of parallel electrodes; and
   forming a contiguous cavity passing through said substrate and said metal interconnect structure-containing layer, and said contiguous cavity comprising said nanochannel.

2. The method of claim 1, further comprising disposing a medium located within said contiguous cavity.

3. The method of claim 2, further comprising:
   disposing a first external electrode and a second external electrode on said medium said first external electrode being disposed above a top surface of said substrate and said second external electrode being disposed below said top surface of said substrate; and
   electrically biasing said first external electrode and said second external electrode with respect to each other to induce flow of electrically charged material through said nanochannel.

4. The method of claim 3, further comprising connecting a leakage current measurement circuitry to said conductive structures, said leakage current measurement circuitry is configured to measure a leakage current through said pair of parallel electrodes and a portion of said electrically charged material within said nanochannel.

5. The method of claim 1, wherein said nanochannel is defined by a rectangular periphery having a width in a range from 0.5 nm to 100 nm, and a length L that is greater than said width, said width being perpendicular to a lengthwise direction of said semiconductor fins and said length being parallel to said lengthwise direction.

6. The method of claim 1, further comprising forming raised active regions on said pair of parallel electrodes by depositing a doped semiconductor material, wherein said nanochannel is defined by a periphery including edges of said raised active regions.

7. The method of claim 6, wherein said periphery further includes a portion of a sidewall of a dielectric material layer located within said metal interconnect structure-containing layer, said sidewall being a surface defining a lateral extent of said contiguous cavity.

8. The method of claim 6, further comprising:
   forming an additional semiconductor fin on said substrate; and
   forming a raised inactive region located on said additional semiconductor fin, said inactive region, including an intrinsic semiconductor material.

9. The method of claim 1, further comprising forming. at least one gate structure straddling said pair of parallel electrodes, wherein a periphery of said nanochannel includes an edge of one of said at least one gate structure.

10. The method of claim 1, wherein a portion of said contiguous cavity above said substrate is formed by etching a region of said at least one dielectric material layer over said pair of parallel electrodes such that sidewalls within said contiguous cavity vertically extend from a topmost surface of said contiguous cavity to a surface selected from a horizontal surface of said substrate and. a surface of said pair of parallel electrodes.

* * * * *